United States Patent
Jones et al.

(10) Patent No.: US 7,494,651 B2
(45) Date of Patent: Feb. 24, 2009

(54) TGF-β BINDING ANTIBODIES

(75) Inventors: Bryan Edward Jones, Carmel, IN (US);
James D. Pancook, San Diego, CA (US); Scott William Rowlinson, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 12/096,383

(22) PCT Filed: Dec. 20, 2006

(86) PCT No.: PCT/US2006/062397

§ 371 (c)(1),
(2), (4) Date: Jun. 6, 2008

(87) PCT Pub. No.: WO2007/076391

PCT Pub. Date: Jul. 5, 2007

(65) Prior Publication Data

US 2008/0292638 A1      Nov. 27, 2008

Related U.S. Application Data

(60) Provisional application No. 60/753,956, filed on Dec. 23, 2005.

(51) Int. Cl.
*A61K 39/395* (2006.01)
*C07K 16/22* (2006.01)

(52) U.S. Cl. .............. 424/145.1; 424/130.1; 424/133.1; 424/141.1; 424/152.1; 424/158.1; 530/387.1; 530/387.3; 530/388.2; 530/388.24

(58) Field of Classification Search ....................... None
See application file for complete search history.

(56) References Cited

FOREIGN PATENT DOCUMENTS

WO      WO2005/097832      10/2005

OTHER PUBLICATIONS

Carlsson, et al., "n-CoDer concept: Unique Types of Antibodies for Diagnostic Use and Therapy," *Expert Review of Molecular Diagnostics* 1(1):102-108 (2001).
Carruthers, et al., "In vitro and in vivo characterization of CAT-192 and 1D11: Neutralising antibodies to transforming growth factor beta," *British Journal of Pharamcology* 135(Proceedings Supp.):265p (Mar. 2002).
Hoefer, et al., "Anti-(Transforming Growth Factor Beta) Antibodies with Predefined Specificity Inhibit Metastasis of Highly Tumorigenic Human Xenotransplants in Nu/Nu Mice," *Cancer Immunology and Immunotherapy* 41(5):302-308 (1995).
Shah, et al., "Neutralisation of TGF-Beta1 and TGF-Beta2 or Exogenous Addition of TGF-Beta3 to Cutaneous Rat Wounds Reduces Scarring," *Journal of Cell Science* 108(Part 3):985-1002 (1995).
Wolleheim, et al., "Sixth International Workshop on Scleroderma Research," *Arthritis Research* 33:34-40 (2001).
PCT International Search Report for PCT/US2006/062397, mailed May 7, 2007.

*Primary Examiner*—Phillip Gambel
(74) *Attorney, Agent, or Firm*—Congping Xie; Charles E. Cohen

(57) ABSTRACT

The present invention provides very high affinity antibodies, or antigen-binding fragments thereof, that neutralize mature human TGF-β1, TGF-β2, and TGF-β3. The antibodies of the invention are useful for treating cell proliferative disorders in a mammal.

4 Claims, 3 Drawing Sheets

FIG. 1

A. Light Chain 3A      (SEQ ID NO: 41)
DIQMTQSPSSLSASVGDRVTITCRASESVDFWGNSFMHWYQQKPGKAPKLLIYLASNLESGVPSRFSGSGSGT
DFTLTISSLQPEDFATYYCQQNIEDPLTFGGGTKVEIK 12.4    (SEQ ID NO: 43)
DIQMTQSPSSLSASVGDRVTITCRASESVDWWGNSFMHWYQQKPGKAPKLLIYLASNLESGVPSRFSGSGSGT
DFTLTISSLQPEDFATYYCQQNIEDPLTFGGGTKVEIK 12.7    (SEQ ID NO: 45)
DIQMTQSPSSLSASVGDRVTITCRASESVDFYGNSFMHWYQQKPGKAPKLLIYLASNLESGVPSRFSGSGSGT
DFTLTISSLQPEDFATYYCQQNIEDPLTFGGGTKVEIK 12.8    (SEQ ID NO: 46)
DIQMTQSPSSLSASVGDRVTITCRASESVDWYGNSFMHWYQQKPGKAPKLLIYYASNLESGVPSRFSGSGSGT
DFTLTISSLQPEDFATYYCQQNAEDPLTFGGGTKVEIK 4.17    (SEQ ID NO: 50)
DIQMTQSPSSLSASVGDRVTITCRASESVDFWGNSFMHWYQQKPGKAPKLLIYLASNLESGVPSRFSGSGSG
TDFTLTISSLQPEDFATYYCQQNAEDPLTFGGGTKVEIK B. Heavy Chain 3A      (SEQ ID NO: 64)
QVQLVQSGAEVKKPGASVKVSCKASGYTFTSYWMNWVRQAPGQGLEWMGQIFPASGSTNYGEMFEGRVTMTT
DTSTSTAYMELRSLRSDDTAVYYCARGIGNYALDAMDYWGQGTLVTVSS 12.4    (SEQ ID NO: 68)
QVQLVQSGAEVKKPGASVKVSCKASGYTFTSYWMNWVRQAPGQGLEWMGQIFPALGSTNYGEMFEGRVTMT
TDTSTSTAYMELRSLRSDDTAVYYCARGIGNYALDAMDYWGQGTLVTVSS 12.7    (SEQ ID NO: 69)
QVQLVQSGAEVKKPGASVKVSCKASGYTFTSEWMNWVRQAPGQGLEWMGQIFPALGSTNYNEMYEGRVTMTT
DTSTSTAYMELRSLRSDDTAVYYCARGIGNYALDAMDYWGQGTLVTVSS 12.8    (SEQ ID NO: 70)
QVQLVQSGAEVKKPGASVKVSCKASGYTFTSYWMNWVRQAPGQGLEWMGQIFPALGSTNYNEMFEGRVTMTT
DTSTSTAYMELRSLRSDDTAVYYCARGIGNYALDAMDYWGQGTLVTVSS 4.17    (SEQ ID NO: 74)
QVQLVQSGAEVKKPGASVKVSCKASGYTFTSYWMNWVRQAPGQGLEWMGQIFPFSGSTNYNEMFEGRVTMTT
DTSTSTAYMELRSLRSDDTAVYYCARGIGNYALDAMDYWGQGTLVTVSS

FIG. 2

A.  Light Chain CDRs

| Name | CDRL1 | CDRL2 | CDRL3 |
|---|---|---|---|
| 3A | RASESVDFWGNSFMH (SEQ ID NO: 88) | LASNLES (SEQ ID NO: 89) | QQNIEDPLT (SEQ ID NO: 90) |
| 12.4 | RASESVDWWGNSFMH (SEQ ID NO: 91) | LASNLES (SEQ ID NO: 89) | QQNIEDPLT (SEQ ID NO: 90) |
| 12.7 | RASESVDFYGNSFMH (SEQ ID NO: 92) | LASNLES (SEQ ID NO: 89) | QQNIEDPLT (SEQ ID NO: 90) |
| 12.8 | RASESVDWYGNSFMH (SEQ ID NO: 93) | YASNLES (SEQ ID NO: 94) | QQNAEDPLT (SEQ ID NO: 95) |
| 4.17 | RASESVDFWGNSFMH (SEQ ID NO: 88) | LASNLES (SEQ ID NO: 89) | QQNAEDPLT (SEQ ID NO: 95) |

B.  Heavy Chain CDRs

| Name | CDRH1 | CDRH2 | CDRH3 |
|---|---|---|---|
| 3A | SYWMN (SEQ ID NO: 96) | QIFPASGSTNYGEMFEG (SEQ ID NO: 97) | GIGNYALDAMDY (SEQ ID NO: 98) |
| 12.4 | SYWMN (SEQ ID NO: 96) | QIFPALGSTNYGEMFEG (SEQ ID NO: 99) | GIGNYALDAMDY (SEQ ID NO: 98) |
| 12.7 | SEWMN (SEQ ID NO: 100) | QIFPALGSTNYNEMYEG (SEQ ID NO: 101) | GIGNYALDAMDY (SEQ ID NO: 98) |
| 12.8 | SYWMN (SEQ ID NO: 96) | QIFPALGSTNYNEMFEG (SEQ ID NO: 101) | GIGNYALDAMDY (SEQ ID NO: 98) |
| 4.17 | SYWMN (SEQ ID NO: 96) | QIFPFSGSTNYNEMFEG (SEQ ID NO: 102) | GIGNYALDAMDY (SEQ ID NO: 98) |

Fig. 3

12.7- Light Chain:
DIQMTQSPSSLSASVGDRVTITCRASESVDFYGNSFMHWYQQKPGKAPKLLIYLASNLESGVPSRFSGSGSG
TDFTLTISSLQPEDFATYYCQQNIEDPLTFGGGTKVEIKRTVAAPSVFIFPPSDEQLKSGTASVVCLLNNFY
PREAKVQWKVDNALQSGNSQESVTEQDSKDSTYSLSSTLTLSKADYEKHKVYACEVTHQGLSSPVTKSFNRG
EC (SEQ ID NO: 80)

12.7-Heavy Chain:
QVQLVQSGAEVKKPGASVKVSCKASGYTFTSEWMNWVRQAPGQGLEWMGQIFPALGSTNYNEMYEGRVTMTT
DTSTSTAYMELRSLRSDDTAVYYCARGIGNYALDAMDYWGQGTLVTVSSASTKGPSVFPLAPCSRSTSESTA
ALGCLVKDYFPEPVTVSWNSGALTSGVHTFPAVLQSSGLYSLSSVVTVPSSSLGTKTYTCNVDHKPSNTKVD
KRVESKYGPPCPPCPAPEFLGGPSVFLFPPKPKDTLMISRTPEVTCVVVDVSQEDPEVQFNWYVDGVEVHNA
KTKPREEQFNSTYRVVSVLTVLHQDWLNGKEYKCKVSNKGLPSSIEKTISKAKGQPREPQVYTLPPSQEEMT
KNQVSLTCLVKGFYPSDIAVEWESNGQPENNYKTTPPVLDSDGSFFLYSRLTVDKSRWQEGNVFSCSVMHEA
LHNHYTQKSLSLSLG (SEQ ID NO: 81)

SEQUENCE LISTING

<160> NUMBER OF SEQ ID NOS: 112

<210> SEQ ID NO 1
<211> LENGTH: 112
<212> TYPE: PRT
<213> ORGANISM: homo sapiens

<400> SEQUENCE: 1

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 2
<211> LENGTH: 112
<212> TYPE: PRT
<213> ORGANISM: homo sapiens

<400> SEQUENCE: 2

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp Lys Trp
            20                  25                  30

Ile His Glu Pro Lys Gly Tyr Asn Ala Asn Phe Cys Ala Gly Ala Cys
        35                  40                  45

Pro Tyr Leu Trp Ser Ser Asp Thr Gln His Ser Arg Val Leu Ser Leu
    50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110

<210> SEQ ID NO 3
<211> LENGTH: 112
<212> TYPE: PRT
<213> ORGANISM: homo sapiens

<400> SEQUENCE: 3

Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

```
Pro Tyr Leu Arg Ser Ala Asp Thr Thr His Ser Thr Val Leu Gly Leu
 50                  55                  60

Tyr Asn Thr Leu Asn Pro Glu Ala Ser Ala Ser Pro Cys Cys Val Pro
 65                  70                  75                  80

Gln Asp Leu Glu Pro Leu Thr Ile Leu Tyr Tyr Val Gly Arg Thr Pro
             85                  90                  95

Lys Val Glu Gln Leu Ser Asn Met Val Val Lys Ser Cys Lys Cys Ser
100                 105                 110

<210> SEQ ID NO 4
<211> LENGTH: 5
<212> TYPE: PRT
<213> ORGANISM: Artificial
<220> FEATURE:
<223> OTHER INFORMATION: synthetic construct

<400> SEQUENCE: 4

Thr Tyr Trp Met Asn
1               5

<210> SEQ ID NO 5
<211> LENGTH: 17
<212> TYPE: PRT
<213> ORGANISM: Artificial
<220> FEATURE:
<223> OTHER INFORMATION: synthetic construct

<400> SEQUENCE: 5

Gln Ile Phe Pro Ala Ser Gly Ser Thr Asn Tyr Asn Glu Met Phe Glu
1               5                   10                  15

Gly

<210> SEQ ID NO 6
<211> LENGTH: 12
<212> TYPE: PRT
<213> ORGANISM: Artificial
<220> FEATURE:
<223> OTHER INFORMATION: synthetic construct

<400> SEQUENCE: 6

Gly Asp Gly Asn Tyr Ala Leu Asp Ala Met Asp Tyr
1               5                   10

<210> SEQ ID NO 7
<211> LENGTH: 15
<212> TYPE: PRT
<213> ORGANISM: Artificial
<220> FEATURE:
<223> OTHER INFORMATION: synthetic construct

<400> SEQUENCE: 7

Arg Ala Ser Glu Ser Val Asp Ser Tyr Gly Asn Ser Phe Met His
1               5                   10                  15

<210> SEQ ID NO 8
<211> LENGTH: 7
<212> TYPE: PRT
<213> ORGANISM: Artificial
<220> FEATURE:
<223> OTHER INFORMATION: synthetic construct

<400> SEQUENCE: 8

Leu Ala Ser Asn Leu Glu Ser
1               5
```

```
<210> SEQ ID NO 9
<211> LENGTH: 9
<212> TYPE: PRT
<213> ORGANISM: Artificial
<220> FEATURE:
<223> OTHER INFORMATION: synthetic construct

<400> SEQUENCE: 9

Gln Gln Asn Asn Glu Asp Pro Leu Thr
1               5

<210> SEQ ID NO 10
<211> LENGTH: 5
<212> TYPE: PRT
<213> ORGANISM: Artificial
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa at position 1 = Thr or Ser
<220> FEATURE:
<221> NAME/KEY: MISC_FEATURE
<222> LOCATION: (2)..(2)
<223> OTHER INFORMATION: Xaa at position 2 = Glu or Tyr

<400> SEQUENCE: 10

Xaa Xaa Trp Met Asn
1               5

<210> SEQ ID NO 11
<211> LENGTH: 17
<212> TYPE: PRT
<213> ORGANISM: Artificial
<220> FEATURE:
<223> OTHER INFORMATION: synthetic construct
<220> FEATURE:
<221> NAME/KEY: MISC_FEATURE
<222> LOCATION: (5)..(5)
<223> OTHER INFORMATION: Xaa at position 5 = Ala or Phe
<220> FEATURE:
<221> NAME/KEY: MISC_FEATURE
<222> LOCATION: (6)..(6)
<223> OTHER INFORMATION: Xaa at position 6 = Ser, Thr, or Leu
<220> FEATURE:
<221> NAME/KEY: MISC_FEATURE
<222> LOCATION: (12)..(12)
<223> OTHER INFORMATION: Xaa at position 12 = Asn, Gly, Ser, Asp, or Ala
<220> FEATURE:
<221> NAME/KEY: MISC_FEATURE
<222> LOCATION: (15)..(15)
<223> OTHER INFORMATION: Xaa at position 15 = Phe or Tyr

<400> SEQUENCE: 11

Gln Ile Phe Pro Xaa Xaa Gly Ser Thr Asn Tyr Xaa Glu Met Xaa Glu
1               5                   10                  15

Gly

<210> SEQ ID NO 12
<211> LENGTH: 12
<212> TYPE: PRT
<213> ORGANISM: Artificial
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa at position 2 = Asp, Ile, Met, Tyr, Leu,
      Val, Gln, or Phe

<400> SEQUENCE: 12
```

Gly Xaa Gly Asn Tyr Ala Leu Asp Ala Met Asp Tyr
1               5                   10

<210> SEQ ID NO 13
<211> LENGTH: 15
<212> TYPE: PRT
<213> ORGANISM: Artificial
<220> FEATURE:
<223> OTHER INFORMATION: synthetic construct
<220> FEATURE:
<221> NAME/KEY: MISC_FEATURE
<222> LOCATION: (8)..(8)
<223> OTHER INFORMATION: Xaa at position 8 = Ser, Tyr, Phe, or Leu
<220> FEATURE:
<221> NAME/KEY: MISC_FEATURE
<222> LOCATION: (9)..(9)
<223> OTHER INFORMATION: Xaa at position 9 = Tyr or Trp

<400> SEQUENCE: 13

Arg Ala Ser Glu Ser Val Asp Xaa Xaa Gly Asn Ser Phe Met His
1               5                   10                  15

<210> SEQ ID NO 14
<211> LENGTH: 7
<212> TYPE: PRT
<213> ORGANISM: Artificial
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa at position 1 = Leu or Tyr

<400> SEQUENCE: 14

Xaa Ala Ser Asn Leu Glu Ser
1               5

<210> SEQ ID NO 15
<211> LENGTH: 9
<212> TYPE: PRT
<213> ORGANISM: Artificial
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa at position 1 = Gln, Thr, or Cys
<220> FEATURE:
<221> NAME/KEY: MISC_FEATURE
<222> LOCATION: (3)..(3)
<223> OTHER INFORMATION: Xaa at position 3 = Asn or His
<220> FEATURE:
<221> NAME/KEY: MISC_FEATURE
<222> LOCATION: (4)..(4)
<223> OTHER INFORMATION: Xaa at position 4 = Asn, Ile, Met, Asp, Thr,
      or Ala

<400> SEQUENCE: 15

Xaa Gln Xaa Xaa Glu Asp Pro Leu Thr
1               5

<210> SEQ ID NO 16
<211> LENGTH: 30
<212> TYPE: PRT
<213> ORGANISM: homo sapiens

<400> SEQUENCE: 16

Gln Val Gln Leu Val Gln Ser Gly Ala Glu Val Lys Lys Pro Gly Ala
1               5                   10                  15

```
Ser Val Lys Val Ser Cys Lys Ala Ser Gly Tyr Thr Phe Thr
 20                  25                  30
```

<210> SEQ ID NO 17
<211> LENGTH: 14
<212> TYPE: PRT
<213> ORGANISM: homo sapiens

<400> SEQUENCE: 17

```
Trp Val Arg Gln Ala Pro Gly Gln Gly Leu Glu Trp Met Gly
  1               5                  10
```

<210> SEQ ID NO 18
<211> LENGTH: 32
<212> TYPE: PRT
<213> ORGANISM: homo sapiens

<400> SEQUENCE: 18

```
Arg Val Thr Met Thr Thr Asp Thr Ser Thr Ser Thr Ala Tyr Met Glu
  1               5                  10                  15

Leu Arg Ser Leu Arg Ser Asp Asp Thr Ala Val Tyr Tyr Cys Ala Arg
 20                  25                  30
```

<210> SEQ ID NO 19
<211> LENGTH: 11
<212> TYPE: PRT
<213> ORGANISM: homo sapiens

<400> SEQUENCE: 19

```
Trp Gly Gln Gly Thr Leu Val Thr Val Ser Ser
  1               5                  10
```

<210> SEQ ID NO 20
<211> LENGTH: 23
<212> TYPE: PRT
<213> ORGANISM: homo sapiens

<400> SEQUENCE: 20

```
Asp Ile Gln Met Thr Gln Ser Pro Ser Ser Leu Ser Ala Ser Val Gly
  1               5                  10                  15

Asp Arg Val Thr Ile Thr Cys
 20
```

<210> SEQ ID NO 21
<211> LENGTH: 15
<212> TYPE: PRT
<213> ORGANISM: homo sapiens

<400> SEQUENCE: 21

```
Trp Tyr Gln Gln Lys Pro Gly Lys Ala Pro Lys Leu Leu Ile Tyr
  1               5                  10                  15
```

<210> SEQ ID NO 22
<211> LENGTH: 32
<212> TYPE: PRT
<213> ORGANISM: homo sapiens

<400> SEQUENCE: 22

```
Gly Val Pro Ser Arg Phe Ser Gly Ser Gly Ser Gly Thr Asp Phe Thr
  1               5                  10                  15

Leu Thr Ile Ser Ser Leu Gln Pro Glu Asp Phe Ala Thr Tyr Tyr Cys
 20                  25                  30
```

<210> SEQ ID NO 23
<211> LENGTH: 10
<212> TYPE: PRT
<213> ORGANISM: homo sapiens

<400> SEQUENCE: 23

Phe Gly Gly Gly Thr Lys Val Glu Ile Lys
1               5                   10

<210> SEQ ID NO 24
<211> LENGTH: 328
<212> TYPE: PRT
<213> ORGANISM: homo sapiens

<400> SEQUENCE: 24

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Lys
                85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly
                325

<210> SEQ ID NO 25
<211> LENGTH: 326
<212> TYPE: PRT
<213> ORGANISM: homo sapiens

<400> SEQUENCE: 25

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
325

<210> SEQ ID NO 26
<211> LENGTH: 107
<212> TYPE: PRT
<213> ORGANISM: homo sapiens

```
<400> SEQUENCE: 26

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 27
<211> LENGTH: 111
<212> TYPE: PRT
<213> ORGANISM: Artificial
<220> FEATURE:
<223> OTHER INFORMATION: synthetic construct

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Tyr
            20                  25                  30

Gly Asn Ser Phe Met His Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Ile
                85                  90                  95

Glu Asp Pro Leu Thr Phe Gly Gly Gly Thr Lys Val Glu Ile Lys
            100                 105                 110

<210> SEQ ID NO 28
<211> LENGTH: 111
<212> TYPE: PRT
<213> ORGANISM: Artificial
<220> FEATURE:
<223> OTHER INFORMATION: synthetic construct

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Tyr
            20                  25                  30

Gly Asn Ser Phe Met His Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80
```

```
Ser Leu Gln Pro Glu Asp Phe Ala Thr Tyr Tyr Cys Gln Gln Asn Met
 85                  90                  95

Glu Asp Pro Leu Thr Phe Gly Gly Gly Thr Lys Val Glu Ile Lys
100                 105                 110
```

<210> SEQ ID NO 29
<211> LENGTH: 111
<212> TYPE: PRT
<213> ORGANISM: Artificial
<220> FEATURE:
<223> OTHER INFORMATION: synthetic construct

<400> SEQUENCE: 29

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Glu Ser Val Asp Ser Tyr
         20                  25                  30

Gly Asn Ser Phe Met His Trp Tyr Gln Gln Lys Pro Gly Lys Ala Pro
     35                  40                  45

Lys Leu Leu Ile Tyr Leu Ala Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Thr Gln Asn Asn
 85                  90                  95

Glu Asp Pro Leu Thr Phe Gly Gly Gly Thr Lys Val Glu Ile Lys
100                 105                 110
```

<210> SEQ ID NO 30
<211> LENGTH: 111
<212> TYPE: PRT
<213> ORGANISM: Artificial
<220> FEATURE:
<223> OTHER INFORMATION: synthetic construct

<400> SEQUENCE: 30

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Glu Ser Val Asp Ser Tyr
         20                  25                  30

Gly Asn Ser Phe Met His Trp Tyr Gln Gln Lys Pro Gly Lys Ala Pro
     35                  40                  45

Lys Leu Leu Ile Tyr Leu Ala Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Asn Asn
 85                  90                  95

Glu Cys Pro Leu Thr Phe Gly Gly Gly Thr Lys Val Glu Ile Lys
100                 105                 110
```

<210> SEQ ID NO 31
<211> LENGTH: 111
<212> TYPE: PRT
<213> ORGANISM: Artificial
<220> FEATURE:
<223> OTHER INFORMATION: synthetic construct

<400> SEQUENCE: 31

```
Asp Ile Gln Met Thr Gln Ser Pro Ser Ser Leu Ser Ala Ser Val Gly
```

```
                1               5                  10                 15
Asp Arg Val Thr Ile Thr Cys Arg Ala Ser Glu Ser Val Asp Ser Tyr
20                  25                  30

Gly Asn Ser Phe Met His Trp Tyr Gln Gln Lys Pro Gly Lys Ala Pro
35                  40                  45

Lys Leu Leu Ile Tyr Leu Ala Ser Asn Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Asp
85                  90                  95

Glu Asp Pro Leu Thr Phe Gly Gly Gly Thr Lys Val Glu Ile Lys
100                 105                 110

<210> SEQ ID NO 32
<211> LENGTH: 111
<212> TYPE: PRT
<213> ORGANISM: Artificial
<220> FEATURE:
<223> OTHER INFORMATION: synthetic construct

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Tyr
20                  25                  30

Gly Asn Ser Phe Met His Trp Tyr Gln Gln Lys Pro Gly Lys Ala Pro
35                  40                  45

Lys Leu Leu Ile Tyr Leu Ala Ser Asn Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Thr
85                  90                  95

Glu Asp Pro Leu Thr Phe Gly Gly Gly Thr Lys Val Glu Ile Lys
100                 105                 110

<210> SEQ ID NO 33
<211> LENGTH: 111
<212> TYPE: PRT
<213> ORGANISM: Artificial
<220> FEATURE:
<223> OTHER INFORMATION: synthetic construct

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Tyr
20                  25                  30

Gly Asn Ser Phe Met His Trp Tyr Gln Gln Lys Pro Gly Lys Ala Pro
35                  40                  45

Lys Leu Leu Ile Tyr Leu Ala Ser Asn Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Asn
85                  90                  95
```

Glu Ile Pro Leu Thr Phe Gly Gly Gly Thr Lys Val Glu Ile Lys
100             105             110

<210> SEQ ID NO 34
<211> LENGTH: 111
<212> TYPE: PRT
<213> ORGANISM: Artificial
<220> FEATURE:
<223> OTHER INFORMATION: synthetic construct

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Tyr
            20                  25                  30

Gly Asn Ser Phe Met His Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Ala
                85                  90                  95

Glu Asp Pro Leu Thr Phe Gly Gly Gly Thr Lys Val Glu Ile Lys
100             105             110

<210> SEQ ID NO 35
<211> LENGTH: 111
<212> TYPE: PRT
<213> ORGANISM: Artificial
<220> FEATURE:
<223> OTHER INFORMATION: synthetic construct

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Tyr
            20                  25                  30

Gly Asn Ser Phe Met His Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Asn
                85                  90                  95

Glu Asp Pro Leu Thr Phe Gly Gly Gly Thr Lys Val Glu Ile Lys
100             105             110

<210> SEQ ID NO 36
<211> LENGTH: 111
<212> TYPE: PRT
<213> ORGANISM: Artificial
<220> FEATURE:
<223> OTHER INFORMATION: synthetic construct

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Trp Tyr

Gly Asn Ser Phe Met His Trp Tyr Gln Gln Lys Pro Gly Lys Ala Pro
35              40                  45

Lys Leu Leu Ile Tyr Leu Ala Ser Asn Leu Glu Ser Gly Val Pro Ser
50              55                  60

Arg Phe Ser Gly Ser Gly Ser Gly Thr Asp Phe Thr Leu Thr Ile Ser
65              70                  75                  80

Ser Leu Gln Pro Glu Asp Phe Ala Thr Tyr Tyr Cys Gln Gln Asn Ile
85              90                  95

Glu Asp Pro Leu Thr Phe Gly Gly Gly Thr Lys Val Glu Ile Lys
100             105                 110

<210> SEQ ID NO 37
<211> LENGTH: 111
<212> TYPE: PRT
<213> ORGANISM: Artificial
<220> FEATURE:
<223> OTHER INFORMATION: synthetic construct

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Phe Tyr
20              25                  30

Gly Asn Ser Phe Met His Trp Tyr Gln Gln Lys Pro Gly Lys Ala Pro
35              40                  45

Lys Leu Leu Ile Tyr Leu Ala Ser Asn Leu Glu Ser Gly Val Pro Ser
50              55                  60

Arg Phe Ser Gly Ser Gly Ser Gly Thr Asp Phe Thr Leu Thr Ile Ser
65              70                  75                  80

Ser Leu Gln Pro Glu Asp Phe Ala Thr Tyr Tyr Cys Gln Gln Asn Ile
85              90                  95

Glu Asp Pro Leu Thr Phe Gly Gly Gly Thr Lys Val Glu Ile Lys
100             105                 110

<210> SEQ ID NO 38
<211> LENGTH: 111
<212> TYPE: PRT
<213> ORGANISM: Artificial
<220> FEATURE:
<223> OTHER INFORMATION: synthetic construct

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Leu Tyr
20              25                  30

Gly Asn Ser Phe Met His Trp Tyr Gln Gln Lys Pro Gly Lys Ala Pro
35              40                  45

Lys Leu Leu Ile Tyr Leu Ala Ser Asn Leu Glu Ser Gly Val Pro Ser
50              55                  60

Arg Phe Ser Gly Ser Gly Ser Gly Thr Asp Phe Thr Leu Thr Ile Ser
65              70                  75                  80

Ser Leu Gln Pro Glu Asp Phe Ala Thr Tyr Tyr Cys Gln Gln Asn Ile
85              90                  95

Glu Asp Pro Leu Thr Phe Gly Gly Gly Thr Lys Val Glu Ile Lys
100             105                 110

```
<210> SEQ ID NO 39
<211> LENGTH: 111
<212> TYPE: PRT
<213> ORGANISM: Artificial
<220> FEATURE:
<223> OTHER INFORMATION: synthetic construct

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Trp
            20                  25                  30

Gly Asn Ser Phe Met His Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Ile
                85                  90                  95

Glu Asp Pro Leu Thr Phe Gly Gly Gly Thr Lys Val Glu Ile Lys
            100                 105                 110

<210> SEQ ID NO 40
<211> LENGTH: 111
<212> TYPE: PRT
<213> ORGANISM: Artificial
<220> FEATURE:
<223> OTHER INFORMATION: synthetic construct

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Tyr
            20                  25                  30

Gly Asn Ser Phe Met His Trp Tyr Gln Gln Lys Pro Gly Lys Ala Pro
        35                  40                  45

Lys Leu Leu Ile Tyr Tyr Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Ile
                85                  90                  95

Glu Asp Pro Leu Thr Phe Gly Gly Gly Thr Lys Val Glu Ile Lys
            100                 105                 110

<210> SEQ ID NO 41
<211> LENGTH: 111
<212> TYPE: PRT
<213> ORGANISM: Artificial
<220> FEATURE:
<223> OTHER INFORMATION: synthetic construct

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Phe Tyr
            20                  25                  30

Gly Asn Ser Phe Met His Trp Tyr Gln Gln Lys Pro Gly Lys Ala Pro
```

```
                35                  40                  45
Lys Leu Leu Ile Tyr Leu Ala Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Asn Ile
             85                  90                  95

Glu Asp Pro Leu Thr Phe Gly Gly Gly Thr Lys Val Glu Ile Lys
        100                 105                 110
```

<210> SEQ ID NO 42
<211> LENGTH: 111
<212> TYPE: PRT
<213> ORGANISM: Artificial
<220> FEATURE:
<223> OTHER INFORMATION: synthetic construct

<400> SEQUENCE: 42

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Glu Ser Val Asp Ser Tyr
             20                  25                  30

Gly Asn Ser Phe Met His Trp Tyr Gln Gln Lys Pro Gly Lys Ala Pro
 35                  40                  45

Lys Leu Leu Ile Tyr Leu Ala Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Asn Ala
             85                  90                  95

Glu Asp Pro Leu Thr Phe Gly Gly Gly Thr Lys Val Glu Ile Lys
        100                 105                 110
```

<210> SEQ ID NO 43
<211> LENGTH: 111
<212> TYPE: PRT
<213> ORGANISM: Artificial
<220> FEATURE:
<223> OTHER INFORMATION: synthetic construct

<400> SEQUENCE: 43

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Glu Ser Val Asp Trp Trp
             20                  25                  30

Gly Asn Ser Phe Met His Trp Tyr Gln Gln Lys Pro Gly Lys Ala Pro
 35                  40                  45

Lys Leu Leu Ile Tyr Leu Ala Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Asn Ile
             85                  90                  95

Glu Asp Pro Leu Thr Phe Gly Gly Gly Thr Lys Val Glu Ile Lys
        100                 105                 110
```

<210> SEQ ID NO 44
<211> LENGTH: 111

<212> TYPE: PRT
<213> ORGANISM: Artificial
<220> FEATURE:
<223> OTHER INFORMATION: synthetic construct

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Tyr
            20                  25                  30

Gly Asn Ser Phe Met His Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Ile
                85                  90                  95

Glu Asp Pro Leu Thr Phe Gly Gly Gly Thr Lys Val Glu Ile Lys
            100                 105                 110

<210> SEQ ID NO 45
<211> LENGTH: 111
<212> TYPE: PRT
<213> ORGANISM: Artificial
<220> FEATURE:
<223> OTHER INFORMATION: synthetic construct

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Phe Tyr
            20                  25                  30

Gly Asn Ser Phe Met His Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Ile
                85                  90                  95

Glu Asp Pro Leu Thr Phe Gly Gly Gly Thr Lys Val Glu Ile Lys
            100                 105                 110

<210> SEQ ID NO 46
<211> LENGTH: 111
<212> TYPE: PRT
<213> ORGANISM: Artificial
<220> FEATURE:
<223> OTHER INFORMATION: synthetic construct

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Trp Tyr
            20                  25                  30

Gly Asn Ser Phe Met His Trp Tyr Gln Gln Lys Pro Gly Lys Ala Pro
        35                  40                  45

Lys Leu Leu Ile Tyr Tyr Ala Ser Asn Leu Glu Ser Gly Val Pro Ser

```
50              55              60

Arg Phe Ser Gly Ser Gly Ser Gly Thr Asp Phe Thr Leu Thr Ile Ser
 65              70              75              80

Ser Leu Gln Pro Glu Asp Phe Ala Thr Tyr Tyr Cys Gln Gln Asn Ala
 85              90              95

Glu Asp Pro Leu Thr Phe Gly Gly Gly Thr Lys Val Glu Ile Lys
100             105             110

<210> SEQ ID NO 47
<211> LENGTH: 111
<212> TYPE: PRT
<213> ORGANISM: Artificial
<220> FEATURE:
<223> OTHER INFORMATION: synthetic construct

<400> SEQUENCE: 47

Asp Ile Gln Met Thr Gln Ser Pro Ser Ser Leu Ser Ala Ser Val Gly
 1               5              10              15

Asp Arg Val Thr Ile Thr Cys Arg Ala Ser Glu Ser Val Asp Ser Tyr
 20              25              30

Gly Asn Ser Phe Met His Trp Tyr Gln Gln Lys Pro Gly Lys Ala Pro
 35              40              45

Lys Leu Leu Ile Tyr Leu Ala Ser Asn Leu Glu Ser Gly Val Pro Ser
 50              55              60

Arg Phe Ser Gly Ser Gly Ser Gly Thr Asp Phe Thr Leu Thr Ile Ser
 65              70              75              80

Ser Leu Gln Pro Glu Asp Phe Ala Thr Tyr Tyr Cys Gln Gln Asn Ile
 85              90              95

Glu Asp Pro Leu Thr Phe Gly Gly Gly Thr Lys Val Glu Ile Lys
100             105             110

<210> SEQ ID NO 48
<211> LENGTH: 111
<212> TYPE: PRT
<213> ORGANISM: Artificial
<220> FEATURE:
<223> OTHER INFORMATION: synthetic construct

<400> SEQUENCE: 48

Asp Ile Gln Met Thr Gln Ser Pro Ser Ser Leu Ser Ala Ser Val Gly
 1               5              10              15

Asp Arg Val Thr Ile Thr Cys Arg Ala Ser Glu Ser Val Asp Ser Tyr
 20              25              30

Gly Asn Ser Phe Met His Trp Tyr Gln Gln Lys Pro Gly Lys Ala Pro
 35              40              45

Lys Leu Leu Ile Tyr Leu Ala Ser Asn Leu Glu Ser Gly Val Pro Ser
 50              55              60

Arg Phe Ser Gly Ser Gly Ser Gly Thr Asp Phe Thr Leu Thr Ile Ser
 65              70              75              80

Ser Leu Gln Pro Glu Asp Phe Ala Thr Tyr Tyr Cys Gln Gln Asn Ile
 85              90              95

Glu Asp Pro Leu Thr Phe Gly Gly Gly Thr Lys Val Glu Ile Lys
100             105             110

<210> SEQ ID NO 49
<211> LENGTH: 111
<212> TYPE: PRT
<213> ORGANISM: Artificial
<220> FEATURE:
```

<223> OTHER INFORMATION: synthetic construct

<400> SEQUENCE: 49

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Phe Trp
            20                  25                  30

Gly Asn Ser Phe Met His Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Ile
                85                  90                  95

Glu Asp Pro Leu Thr Phe Gly Gly Gly Thr Lys Val Glu Ile Lys
            100                 105                 110
```

<210> SEQ ID NO 50
<211> LENGTH: 111
<212> TYPE: PRT
<213> ORGANISM: Artificial
<220> FEATURE:
<223> OTHER INFORMATION: synthetic construct

<400> SEQUENCE: 50

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Phe Trp
            20                  25                  30

Gly Asn Ser Phe Met His Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Ala
                85                  90                  95

Glu Asp Pro Leu Thr Phe Gly Gly Gly Thr Lys Val Glu Ile Lys
            100                 105                 110
```

<210> SEQ ID NO 51
<211> LENGTH: 111
<212> TYPE: PRT
<213> ORGANISM: Artificial
<220> FEATURE:
<223> OTHER INFORMATION: synthetic construct

<400> SEQUENCE: 51

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Phe Tyr
            20                  25                  30

Gly Asn Ser Phe Met His Trp Tyr Gln Gln Lys Pro Gly Lys Ala Pro
        35                  40                  45

Lys Leu Leu Ile Tyr Tyr Ala Ser Asn Leu Glu Ser Gly Val Pro Ser
    50                  55                  60

Arg Phe Ser Gly Ser Gly Ser Gly Thr Asp Phe Thr Leu Thr Ile Ser
```

```
                 65                  70                  75                  80

Ser Leu Gln Pro Glu Asp Phe Ala Thr Tyr Tyr Cys Gln Gln Asn Ile
 85                  90                  95

Glu Asp Pro Leu Thr Phe Gly Gly Gly Thr Lys Val Glu Ile Lys
100                 105                 110

<210> SEQ ID NO 52
<211> LENGTH: 111
<212> TYPE: PRT
<213> ORGANISM: Artificial
<220> FEATURE:
<223> OTHER INFORMATION: synthetic construct

<400> SEQUENCE: 52

Asp Ile Gln Met Thr Gln Ser Pro Ser Ser Leu Ser Ala Ser Val Gly
  1               5                  10                  15

Asp Arg Val Thr Ile Thr Cys Arg Ala Ser Glu Ser Val Asp Phe Trp
 20                  25                  30

Gly Asn Ser Phe Met His Trp Tyr Gln Gln Lys Pro Gly Lys Ala Pro
 35                  40                  45

Lys Leu Leu Ile Tyr Leu Ala Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Asn Ile
 85                  90                  95

Glu Asp Pro Leu Thr Phe Gly Gly Gly Thr Lys Val Glu Ile Lys
100                 105                 110

<210> SEQ ID NO 53
<211> LENGTH: 111
<212> TYPE: PRT
<213> ORGANISM: Artificial
<220> FEATURE:
<223> OTHER INFORMATION: synthetic construct

<400> SEQUENCE: 53

Asp Ile Gln Met Thr Gln Ser Pro Ser Ser Leu Ser Ala Ser Val Gly
  1               5                  10                  15

Asp Arg Val Thr Ile Thr Cys Arg Ala Ser Glu Ser Val Asp Trp Trp
 20                  25                  30

Gly Asn Ser Phe Met His Trp Tyr Gln Gln Lys Pro Gly Lys Ala Pro
 35                  40                  45

Lys Leu Leu Ile Tyr Leu Ala Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Asn Ile
 85                  90                  95

Glu Asp Pro Leu Thr Phe Gly Gly Gly Thr Lys Val Glu Ile Lys
100                 105                 110

<210> SEQ ID NO 54
<211> LENGTH: 111
<212> TYPE: PRT
<213> ORGANISM: Artificial
<220> FEATURE:
<223> OTHER INFORMATION: synthetic construct

<400> SEQUENCE: 54
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Trp Tyr
            20                  25                  30

Gly Asn Ser Phe Met His Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Ile
            85                  90                  95

Glu Asp Pro Leu Thr Phe Gly Gly Gly Thr Lys Val Glu Ile Lys
        100                 105                 110

<210> SEQ ID NO 55
<211> LENGTH: 111
<212> TYPE: PRT
<213> ORGANISM: Artificial
<220> FEATURE:
<223> OTHER INFORMATION: synthetic construct

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Trp Trp
            20                  25                  30

Gly Asn Ser Phe Met His Trp Tyr Gln Gln Lys Pro Gly Lys Ala Pro
        35                  40                  45

Lys Leu Leu Ile Tyr Tyr Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Asn
            85                  90                  95

Glu Asp Pro Leu Thr Phe Gly Gly Gly Thr Lys Val Glu Ile Lys
        100                 105                 110

<210> SEQ ID NO 56
<211> LENGTH: 111
<212> TYPE: PRT
<213> ORGANISM: Artificial
<220> FEATURE:
<223> OTHER INFORMATION: synthetic construct

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Phe Tyr
            20                  25                  30

Gly Asn Ser Phe Met His Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Ile

```
                                       85                  90                  95

Glu Asp Pro Leu Thr Phe Gly Gly Gly Thr Lys Val Glu Ile Lys
100                 105                 110

<210> SEQ ID NO 57
<211> LENGTH: 111
<212> TYPE: PRT
<213> ORGANISM: Artificial
<220> FEATURE:
<223> OTHER INFORMATION: synthetic construct

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Trp Tyr
            20                  25                  30

Gly Asn Ser Phe Met His Trp Tyr Gln Gln Lys Pro Gly Lys Ala Pro
        35                  40                  45

Lys Leu Leu Ile Tyr Tyr Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Ala
                85                  90                  95

Glu Asp Pro Leu Thr Phe Gly Gly Gly Thr Lys Val Glu Ile Lys
100                 105                 110

<210> SEQ ID NO 58
<211> LENGTH: 111
<212> TYPE: PRT
<213> ORGANISM: Artificial
<220> FEATURE:
<223> OTHER INFORMATION: synthetic construct

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Trp Tyr
            20                  25                  30

Gly Asn Ser Phe Met His Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Ile
                85                  90                  95

Glu Asp Pro Leu Thr Phe Gly Gly Gly Thr Lys Val Glu Ile Lys
100                 105                 110

<210> SEQ ID NO 59
<211> LENGTH: 111
<212> TYPE: PRT
<213> ORGANISM: Artificial
<220> FEATURE:
<223> OTHER INFORMATION: synthetic construct

<400> SEQUENCE: 59

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Glu Ser Val Asp Trp Tyr
            20                  25                  30

Gly Asn Ser Phe Met His Trp Tyr Gln Gln Lys Pro Gly Lys Ala Pro
         35                  40                  45

Lys Leu Leu Ile Tyr Tyr Ala Ser Asn Leu Glu Ser Gly Val Pro Ser
     50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Asn Ala
             85                  90                  95

Glu Asp Pro Leu Thr Phe Gly Gly Gly Thr Lys Val Glu Ile Lys
        100                 105                 110

<210> SEQ ID NO 60
<211> LENGTH: 111
<212> TYPE: PRT
<213> ORGANISM: Artificial
<220> FEATURE:
<223> OTHER INFORMATION: synthetic construct

<400> SEQUENCE: 60

Asp Ile Gln Met Thr Gln Ser Pro Ser Ser Leu Ser Ala Ser Val Gly
 1               5                  10                  15

Asp Arg Val Thr Ile Thr Cys Arg Ala Ser Glu Ser Val Asp Trp Trp
            20                  25                  30

Gly Asn Ser Phe Met His Trp Tyr Gln Gln Lys Pro Gly Lys Ala Pro
         35                  40                  45

Lys Leu Leu Ile Tyr Leu Ala Ser Asn Leu Glu Ser Gly Val Pro Ser
     50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Asn Ala
             85                  90                  95

Glu Asp Pro Leu Thr Phe Gly Gly Gly Thr Lys Val Glu Ile Lys
        100                 105                 110

<210> SEQ ID NO 61
<211> LENGTH: 111
<212> TYPE: PRT
<213> ORGANISM: Artificial
<220> FEATURE:
<223> OTHER INFORMATION: synthetic construct

<400> SEQUENCE: 61

Asp Ile Gln Met Thr Gln Ser Pro Ser Ser Leu Ser Ala Ser Val Gly
 1               5                  10                  15

Asp Arg Val Thr Ile Thr Cys Arg Ala Ser Glu Ser Val Asp Ser Trp
            20                  25                  30

Gly Asn Ser Phe Met His Trp Tyr Gln Gln Lys Pro Gly Lys Ala Pro
         35                  40                  45

Lys Leu Leu Ile Tyr Leu Ala Ser Asn Leu Glu Ser Gly Val Pro Ser
     50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Asn Asn
             85                  90                  95

Glu Asp Pro Leu Thr Phe Gly Gly Gly Thr Lys Val Glu Ile Lys

<210> SEQ ID NO 62
<211> LENGTH: 111
<212> TYPE: PRT
<213> ORGANISM: Artificial
<220> FEATURE:
<223> OTHER INFORMATION: synthetic construct

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Trp Trp
            20                  25                  30

Gly Asn Ser Phe Met His Trp Tyr Gln Gln Lys Pro Gly Lys Ala Pro
        35                  40                  45

Lys Leu Leu Ile Tyr Tyr Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Ile
                85                  90                  95

Glu Asp Pro Leu Thr Phe Gly Gly Gly Thr Lys Val Glu Ile Lys
            100                 105                 110

<210> SEQ ID NO 63
<211> LENGTH: 111
<212> TYPE: PRT
<213> ORGANISM: Artificial
<220> FEATURE:
<223> OTHER INFORMATION: synthetic construct

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Phe Trp
            20                  25                  30

Gly Asn Ser Phe Met His Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Ala
                85                  90                  95

Glu Asp Pro Leu Thr Phe Gly Gly Gly Thr Lys Val Glu Ile Lys
            100                 105                 110

<210> SEQ ID NO 64
<211> LENGTH: 121
<212> TYPE: PRT
<213> ORGANISM: Artificial
<220> FEATURE:
<223> OTHER INFORMATION: synthetic construct

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
35                  40                  45

Gly Gln Ile Phe Pro Ala Ser Gly Ser Thr Asn Tyr Gly Glu Met Phe
50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
85                  90                  95

Ala Arg Gly Ile Gly Asn Tyr Ala Leu Asp Ala Met Asp Tyr Trp Gly
100                 105                 110

Gln Gly Thr Leu Val Thr Val Ser Ser
115                 120

<210> SEQ ID NO 65
<211> LENGTH: 121
<212> TYPE: PRT
<213> ORGANISM: Artificial
<220> FEATURE:
<223> OTHER INFORMATION: synthetic construct

<400> SEQUENCE: 65

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
20                  25                  30

Trp Met Asn Trp Val Arg Gln Ala Pro Gly Gln Gly Leu Glu Trp Met
35                  40                  45

Gly Gln Ile Phe Pro Ala Ser Gly Ser Thr Asn Tyr Ser Glu Met Phe
50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
85                  90                  95

Ala Arg Gly Met Gly Asn Tyr Ala Leu Asp Ala Met Asp Tyr Trp Gly
100                 105                 110

Gln Gly Thr Leu Val Thr Val Ser Ser
115                 120

<210> SEQ ID NO 66
<211> LENGTH: 121
<212> TYPE: PRT
<213> ORGANISM: Artificial
<220> FEATURE:
<223> OTHER INFORMATION: synthetic construct

<400> SEQUENCE: 66

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
20                  25                  30

Trp Met Asn Trp Val Arg Gln Ala Pro Gly Gln Gly Leu Glu Trp Met
35                  40                  45

Gly Gln Ile Phe Pro Ala Ser Gly Ser Thr Asn Tyr Gly Glu Met Phe
50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys 85                  90                  95
Ala Arg Gly Ile Gly Asn Tyr Ala Leu Asp Ala Met Asp Tyr Trp Gly
            100                 105                 110

Gln Gly Thr Leu Val Thr Val Ser Ser
        115                 120

<210> SEQ ID NO 67
<211> LENGTH: 121
<212> TYPE: PRT
<213> ORGANISM: Artificial
<220> FEATURE:
<223> OTHER INFORMATION: synthetic construct

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Met Asn Trp Val Arg Gln Ala Pro Gly Gln Gly Leu Glu Trp Met
        35                  40                  45

Gly Gln Ile Phe Pro Ala Ser Gly Ser Thr Asn Tyr Asp Glu Met Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Asn Tyr Ala Leu Asp Ala Met Asp Tyr Trp Gly
            100                 105                 110

Gln Gly Thr Leu Val Thr Val Ser Ser
        115                 120

<210> SEQ ID NO 68
<211> LENGTH: 121
<212> TYPE: PRT
<213> ORGANISM: Artificial
<220> FEATURE:
<223> OTHER INFORMATION: synthetic construct

<400> SEQUENCE: 68

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Gln Ile Phe Pro Ala Leu Gly Ser Thr Asn Tyr Gly Glu Met Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Ile Gly Asn Tyr Ala Leu Asp Ala Met Asp Tyr Trp Gly
            100                 105                 110

Gln Gly Thr Leu Val Thr Val Ser Ser
        115                 120

<210> SEQ ID NO 69
<211> LENGTH: 121

```
<212> TYPE: PRT
<213> ORGANISM: Artificial
<220> FEATURE:
<223> OTHER INFORMATION: synthetic construct

<400> SEQUENCE: 69

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Glu
            20                  25                  30

Trp Met Asn Trp Val Arg Gln Ala Pro Gly Gln Gly Leu Glu Trp Met
        35                  40                  45

Gly Gln Ile Phe Pro Ala Leu Gly Ser Thr Asn Tyr Asn Glu Met Tyr
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Ile Gly Asn Tyr Ala Leu Asp Ala Met Asp Tyr Trp Gly
            100                 105                 110

Gln Gly Thr Leu Val Thr Val Ser Ser
        115                 120

<210> SEQ ID NO 70
<211> LENGTH: 121
<212> TYPE: PRT
<213> ORGANISM: Artificial
<220> FEATURE:
<223> OTHER INFORMATION: synthetic construct

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Gln Ile Phe Pro Ala Leu Gly Ser Thr Asn Tyr Asn Glu Met Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Ile Gly Asn Tyr Ala Leu Asp Ala Met Asp Tyr Trp Gly
            100                 105                 110

Gln Gly Thr Leu Val Thr Val Ser Ser
        115                 120

<210> SEQ ID NO 71
<211> LENGTH: 121
<212> TYPE: PRT
<213> ORGANISM: Artificial
<220> FEATURE:
<223> OTHER INFORMATION: synthetic construct

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
```

```
            20                  25                  30

Trp Met Asn Trp Val Arg Gln Ala Pro Gly Gln Gly Leu Glu Trp Met
 35                  40                  45

Gly Gln Ile Phe Pro Ala Ser Gly Ser Thr Asn Tyr Gly Glu Met Phe
 50                  55                  60

Glu Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
 85                  90                  95

Ala Arg Gly Gln Gly Asn Tyr Ala Leu Asp Ala Met Asp Tyr Trp Gly
100                 105                 110

Gln Gly Thr Leu Val Thr Val Ser Ser
115                 120

<210> SEQ ID NO 72
<211> LENGTH: 121
<212> TYPE: PRT
<213> ORGANISM: Artificial
<220> FEATURE:
<223> OTHER INFORMATION: synthetic construct

<400> SEQUENCE: 72

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Thr Tyr
 20                  25                  30

Trp Met Asn Trp Val Arg Gln Ala Pro Gly Gln Gly Leu Glu Trp Met
 35                  40                  45

Gly Gln Ile Phe Pro Ala Ser Gly Ser Thr Asn Tyr Ala Glu Met Phe
 50                  55                  60

Glu Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
 85                  90                  95

Ala Arg Gly Phe Gly Asn Tyr Ala Leu Asp Ala Met Asp Tyr Trp Gly
100                 105                 110

Gln Gly Thr Leu Val Thr Val Ser Ser
115                 120

<210> SEQ ID NO 73
<211> LENGTH: 121
<212> TYPE: PRT
<213> ORGANISM: Artificial
<220> FEATURE:
<223> OTHER INFORMATION: synthetic construct

<400> SEQUENCE: 73

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Thr Tyr
 20                  25                  30

Trp Met Asn Trp Val Arg Gln Ala Pro Gly Gln Gly Leu Glu Trp Met
 35                  40                  45

Gly Gln Ile Phe Pro Ala Ser Gly Ser Thr Asn Tyr Gly Glu Met Phe
 50                  55                  60

Glu Gly Arg Val Thr Met Thr Thr Asp Thr Ser Thr Ser Thr Ala Tyr
 65                  70                  75                  80
```

```
Met Glu Leu Arg Ser Leu Arg Ser Asp Asp Thr Ala Val Tyr Tyr Cys
 85                  90                  95

Ala Arg Gly Ile Gly Asn Tyr Ala Leu Asp Ala Met Asp Tyr Trp Gly
100                 105                 110

Gln Gly Thr Leu Val Thr Val Ser Ser
115                 120

<210> SEQ ID NO 74
<211> LENGTH: 121
<212> TYPE: PRT
<213> ORGANISM: Artificial
<220> FEATURE:
<223> OTHER INFORMATION: synthetic construct

<400> SEQUENCE: 74

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met Asn Trp Val Arg Gln Ala Pro Gly Gln Gly Leu Glu Trp Met
            35                  40                  45

Gly Gln Ile Phe Pro Phe Ser Gly Ser Thr Asn Tyr Asn Glu Met Phe
        50                  55                  60

Glu Gly Arg Val Thr Met Thr Thr Asp Thr Ser Thr Ser Thr Ala Tyr
    65                  70                  75                  80

Met Glu Leu Arg Ser Leu Arg Ser Asp Asp Thr Ala Val Tyr Tyr Cys
 85                  90                  95

Ala Arg Gly Ile Gly Asn Tyr Ala Leu Asp Ala Met Asp Tyr Trp Gly
100                 105                 110

Gln Gly Thr Leu Val Thr Val Ser Ser
115                 120

<210> SEQ ID NO 75
<211> LENGTH: 121
<212> TYPE: PRT
<213> ORGANISM: Artificial
<220> FEATURE:
<223> OTHER INFORMATION: synthetic construct

<400> SEQUENCE: 75

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
                20                  25                  30

Trp Met Asn Trp Val Arg Gln Ala Pro Gly Gln Gly Leu Glu Trp Met
            35                  40                  45

Gly Gln Ile Phe Pro Ala Ser Gly Ser Thr Asn Tyr Gly Glu Met Phe
        50                  55                  60

Glu Gly Arg Val Thr Met Thr Thr Asp Thr Ser Thr Ser Thr Ala Tyr
    65                  70                  75                  80

Met Glu Leu Arg Ser Leu Arg Ser Asp Asp Thr Ala Val Tyr Tyr Cys
 85                  90                  95

Ala Arg Gly Ile Gly Asn Tyr Ala Leu Asp Ala Met Asp Tyr Trp Gly
100                 105                 110

Gln Gly Thr Leu Val Thr Val Ser Ser
115                 120

<210> SEQ ID NO 76
```

<211> LENGTH: 218
<212> TYPE: PRT
<213> ORGANISM: Artificial
<220> FEATURE:
<223> OTHER INFORMATION: synthetic construct

<400> SEQUENCE: 76

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Phe Trp
            20                  25                  30

Gly Asn Ser Phe Met His Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Ile
                85                  90                  95

Glu Asp Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 77
<211> LENGTH: 447
<212> TYPE: PRT
<213> ORGANISM: Artificial
<220> FEATURE:
<223> OTHER INFORMATION: synthetic construct

<400> SEQUENCE: 77

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Gln Ile Phe Pro Ala Ser Gly Ser Thr Asn Tyr Gly Glu Met Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Ile Gly Asn Tyr Ala Leu Asp Ala Met Asp Tyr Trp Gly
```

```
                100             105                 110
Gln Gly Thr Leu Val Thr Val Ser Ser Ala Ser Thr Lys Gly Pro Ser
115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
165                 170                 175

Val Leu Gln Ser Ser Gly Leu Tyr Ser Leu Ser Ser Val Val Thr Val
180                 185                 190

Pro Ser Ser Ser Leu Gly Thr Lys Thr Tyr Thr Cys Asn Val Asp His
195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
245                 250                 255

Thr Pro Glu Val Thr Cys Val Val Val Asp Val Ser Gln Glu Asp Pro
260                 265                 270

Glu Val Gln Phe Asn Trp Tyr Val Asp Gly Val Glu Val His Asn Ala
275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
325                 330                 335

Ile Ser Lys Ala Lys Gly Gln Pro Arg Glu Pro Gln Val Tyr Thr Leu
340                 345                 350

Pro Pro Ser Gln Glu Glu Met Thr Lys Asn Gln Val Ser Leu Thr Cys
355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
405                 410                 415

Arg Trp Gln Glu Gly Asn Val Phe Ser Cys Ser Val Met His Glu Ala
420                 425                 430

Leu His Asn His Tyr Thr Gln Lys Ser Leu Ser Leu Ser Leu Gly
435                 440                 445

<210> SEQ ID NO 78
<211> LENGTH: 218
<212> TYPE: PRT
<213> ORGANISM: Artificial
<220> FEATURE:
<223> OTHER INFORMATION: synthetic construct

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Trp Trp
```

-continued

```
            20                  25                  30

Gly Asn Ser Phe Met His Trp Tyr Gln Gln Lys Pro Gly Lys Ala Pro
 35                  40                  45

Lys Leu Leu Ile Tyr Leu Ala Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Asn Ile
 85                  90                  95

Glu Asp Pro Leu Thr Phe Gly Gly Gly Thr Lys Val Glu Ile Lys Arg
100                 105                 110

Thr Val Ala Ala Pro Ser Val Phe Ile Phe Pro Pro Ser Asp Glu Gln
115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
165                 170                 175

Tyr Ser Leu Ser Ser Thr Leu Thr Leu Ser Lys Ala Asp Tyr Glu Lys
180                 185                 190

His Lys Val Tyr Ala Cys Glu Val Thr His Gln Gly Leu Ser Ser Pro
195                 200                 205

Val Thr Lys Ser Phe Asn Arg Gly Glu Cys
210                 215

<210> SEQ ID NO 79
<211> LENGTH: 447
<212> TYPE: PRT
<213> ORGANISM: Artificial
<220> FEATURE:
<223> OTHER INFORMATION: synthetic construct

<400> SEQUENCE: 79

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
 20                  25                  30

Trp Met Asn Trp Val Arg Gln Ala Pro Gly Gln Gly Leu Glu Trp Met
 35                  40                  45

Gly Gln Ile Phe Pro Ala Leu Gly Ser Thr Asn Tyr Gly Glu Met Phe
 50                  55                  60

Glu Gly Arg Val Thr Met Thr Thr Asp Thr Ser Thr Thr Ala Tyr
 65                  70                  75                  80

Met Glu Leu Arg Ser Leu Arg Ser Asp Asp Thr Ala Val Tyr Tyr Cys
 85                  90                  95

Ala Arg Gly Ile Gly Asn Tyr Ala Leu Asp Ala Met Asp Tyr Trp Gly
100                 105                 110

Gln Gly Thr Leu Val Thr Val Ser Ser Ala Ser Thr Lys Gly Pro Ser
115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
```

```
                165                 170                 175
Val Leu Gln Ser Ser Gly Leu Tyr Ser Leu Ser Val Val Thr Val
        180                 185                 190

Pro Ser Ser Ser Leu Gly Thr Lys Thr Tyr Thr Cys Asn Val Asp His
    195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
        260                 265                 270

Glu Val Gln Phe Asn Trp Tyr Val Asp Gly Val Glu Val His Asn Ala
    275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Gln Glu Glu Met Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
        420                 425                 430

Leu His Asn His Tyr Thr Gln Lys Ser Leu Ser Leu Ser Leu Gly
    435                 440                 445

<210> SEQ ID NO 80
<211> LENGTH: 218
<212> TYPE: PRT
<213> ORGANISM: Artificial
<220> FEATURE:
<223> OTHER INFORMATION: synthetic construct

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Phe Tyr
            20                  25                  30

Gly Asn Ser Phe Met His Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Ile
```

Glu Asp Pro Leu Thr Phe Gly Gly Gly Thr Lys Val Glu Ile Lys Arg
100                 105                 110

Thr Val Ala Ala Pro Ser Val Phe Ile Phe Pro Pro Ser Asp Glu Gln
115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
165                 170                 175

Tyr Ser Leu Ser Ser Thr Leu Thr Leu Ser Lys Ala Asp Tyr Glu Lys
180                 185                 190

His Lys Val Tyr Ala Cys Glu Val Thr His Gln Gly Leu Ser Ser Pro
195                 200                 205

Val Thr Lys Ser Phe Asn Arg Gly Glu Cys
210                 215

<210> SEQ ID NO 81
<211> LENGTH: 447
<212> TYPE: PRT
<213> ORGANISM: Artificial
<220> FEATURE:
<223> OTHER INFORMATION: synthetic construct

<400> SEQUENCE: 81

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Glu
20                  25                  30

Trp Met Asn Trp Val Arg Gln Ala Pro Gly Gln Gly Leu Glu Trp Met
35                  40                  45

Gly Gln Ile Phe Pro Ala Leu Gly Ser Thr Asn Tyr Asn Glu Met Tyr
50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
85                  90                  95

Ala Arg Gly Ile Gly Asn Tyr Ala Leu Asp Ala Met Asp Tyr Trp Gly
100                 105                 110

Gln Gly Thr Leu Val Thr Val Ser Ser Ala Ser Thr Lys Gly Pro Ser
115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
165                 170                 175

Val Leu Gln Ser Ser Gly Leu Tyr Ser Leu Ser Ser Val Val Thr Val
180                 185                 190

Pro Ser Ser Ser Leu Gly Thr Lys Thr Tyr Thr Cys Asn Val Asp His
195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser

```
                225                 230                 235                 240
Val Phe Leu Phe Pro Pro Lys Pro Lys Asp Thr Leu Met Ile Ser Arg
245                 250                 255

Thr Pro Glu Val Thr Cys Val Val Val Asp Val Ser Gln Glu Asp Pro
260                 265                 270

Glu Val Gln Phe Asn Trp Tyr Val Asp Gly Val Glu Val His Asn Ala
275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
325                 330                 335

Ile Ser Lys Ala Lys Gly Gln Pro Arg Glu Pro Gln Val Tyr Thr Leu
340                 345                 350

Pro Pro Ser Gln Glu Glu Met Thr Lys Asn Gln Val Ser Leu Thr Cys
355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
405                 410                 415

Arg Trp Gln Glu Gly Asn Val Phe Ser Cys Ser Val Met His Glu Ala
420                 425                 430

Leu His Asn His Tyr Thr Gln Lys Ser Leu Ser Leu Ser Leu Gly
435                 440                 445

<210> SEQ ID NO 82
<211> LENGTH: 218
<212> TYPE: PRT
<213> ORGANISM: Artificial
<220> FEATURE:
<223> OTHER INFORMATION: synthetic construct

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Trp Tyr
20                  25                  30

Gly Asn Ser Phe Met His Trp Tyr Gln Gln Lys Pro Gly Lys Ala Pro
35                  40                  45

Lys Leu Leu Ile Tyr Tyr Ala Ser Asn Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Ala
85                  90                  95

Glu Asp Pro Leu Thr Phe Gly Gly Gly Thr Lys Val Glu Ile Lys Arg
100                 105                 110

Thr Val Ala Ala Pro Ser Val Phe Ile Phe Pro Pro Ser Asp Glu Gln
115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
```

-continued

```
                145                 150                 155                 160
Gly Asn Ser Gln Glu Ser Val Thr Glu Gln Asp Ser Lys Asp Ser Thr
165                 170                 175

Tyr Ser Leu Ser Ser Thr Leu Thr Leu Ser Lys Ala Asp Tyr Glu Lys
180                 185                 190

His Lys Val Tyr Ala Cys Glu Val Thr His Gln Gly Leu Ser Ser Pro
195                 200                 205

Val Thr Lys Ser Phe Asn Arg Gly Glu Cys
210                 215

<210> SEQ ID NO 83
<211> LENGTH: 447
<212> TYPE: PRT
<213> ORGANISM: Artificial
<220> FEATURE:
<223> OTHER INFORMATION: synthetic construct

<400> SEQUENCE: 83

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Gln Ile Phe Pro Ala Leu Gly Ser Thr Asn Tyr Asn Glu Met Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Ile Gly Asn Tyr Ala Leu Asp Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
```

```
                290                 295                 300
Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
325                 330                 335

Ile Ser Lys Ala Lys Gly Gln Pro Arg Glu Pro Gln Val Tyr Thr Leu
340                 345                 350

Pro Pro Ser Gln Glu Glu Met Thr Lys Asn Gln Val Ser Leu Thr Cys
355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
405                 410                 415

Arg Trp Gln Glu Gly Asn Val Phe Ser Cys Ser Val Met His Glu Ala
420                 425                 430

Leu His Asn His Tyr Thr Gln Lys Ser Leu Ser Leu Ser Leu Gly
435                 440                 445
```

<210> SEQ ID NO 84
<211> LENGTH: 218
<212> TYPE: PRT
<213> ORGANISM: Artificial
<220> FEATURE:
<223> OTHER INFORMATION: synthetic construct

<400> SEQUENCE: 84

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Phe Trp
                20                  25                  30

Gly Asn Ser Phe Met His Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Ala
                85                  90                  95

Glu Asp Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

-continued 210           215

<210> SEQ ID NO 85
<211> LENGTH: 447
<212> TYPE: PRT
<213> ORGANISM: Artificial
<220> FEATURE:
<223> OTHER INFORMATION: synthetic construct

<400> SEQUENCE: 85

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Gln Ile Phe Pro Phe Ser Gly Ser Thr Asn Tyr Asn Glu Met Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Ile Gly Asn Tyr Ala Leu Asp Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys

```
                                355             360             365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
405                 410                 415

Arg Trp Gln Glu Gly Asn Val Phe Ser Cys Ser Val Met His Glu Ala
420                 425                 430

Leu His Asn His Tyr Thr Gln Lys Ser Leu Ser Leu Ser Leu Gly
435                 440                 445

<210> SEQ ID NO 86
<211> LENGTH: 120
<212> TYPE: PRT
<213> ORGANISM: Artificial
<220> FEATURE:
<223> OTHER INFORMATION: synthetic construct
<220> FEATURE:
<221> NAME/KEY: misc_feature
<222> LOCATION: (31)..(32)
<223> OTHER INFORMATION: Xaa can be any naturally occurring amino acid
<220> FEATURE:
<221> NAME/KEY: misc_feature
<222> LOCATION: (54)..(55)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (99)..(99)
<223> OTHER INFORMATION: Xaa can be any naturally occurring amino acid

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Xaa Xaa
            20                  25                  30

Trp Met Asn Trp Val Arg Gln Ala Pro Gly Gln Gly Leu Glu Trp Met
35                  40                  45

Gly Gln Ile Phe Pro Xaa Xaa Gly Ser Thr Asn Tyr Xaa Glu Met Xaa
50                  55                  60

Glu Gly Val Thr Met Thr Thr Asp Thr Ser Thr Ser Thr Ala Tyr Met
65                  70                  75                  80

Glu Leu Arg Ser Leu Arg Ser Asp Asp Thr Ala Val Tyr Tyr Cys Ala
            85                  90                  95

Arg Gly Xaa Gly Asn Tyr Ala Leu Asp Ala Met Asp Tyr Trp Gly Gln
100                 105                 110

Gly Thr Leu Val Thr Val Ser Ser
115                 120

<210> SEQ ID NO 87
<211> LENGTH: 111
<212> TYPE: PRT
<213> ORGANISM: Artificial
<220> FEATURE:
<223> OTHER INFORMATION: synthetic construct
<220> FEATURE:
```

```
<221> NAME/KEY: misc_feature
<222> LOCATION: (31)..(32)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (95)..(96)
<223> OTHER INFORMATION: Xaa can be any naturally occurring amino acid

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Xaa Xaa
            20                  25                  30

Gly Asn Ser Phe Met His Trp Tyr Gln Gln Lys Pro Gly Lys Ala Pro
        35                  40                  45

Lys Leu Leu Ile Tyr Xaa Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Xaa Gln Xaa Xaa
                85                  90                  95

Glu Asp Pro Leu Thr Phe Gly Gly Gly Thr Lys Val Glu Ile Lys
            100                 105                 110

<210> SEQ ID NO 88
<211> LENGTH: 15
<212> TYPE: PRT
<213> ORGANISM: Artificial
<220> FEATURE:
<223> OTHER INFORMATION: synthetic construct

<400> SEQUENCE: 88

Arg Ala Ser Glu Ser Val Asp Phe Trp Gly Asn Ser Phe Met His
1               5                   10                  15

<210> SEQ ID NO 89
<211> LENGTH: 7
<212> TYPE: PRT
<213> ORGANISM: Artificial
<220> FEATURE:
<223> OTHER INFORMATION: synthetic construct

<400> SEQUENCE: 89

Leu Ala Ser Asn Leu Glu Ser
1               5

<210> SEQ ID NO 90
<211> LENGTH: 9
<212> TYPE: PRT
<213> ORGANISM: Artificial
<220> FEATURE:
<223> OTHER INFORMATION: synthetic construct

<400> SEQUENCE: 90

Gln Gln Asn Ile Glu Asp Pro Leu Thr
1               5
```

<210> SEQ ID NO 91
<211> LENGTH: 15
<212> TYPE: PRT
<213> ORGANISM: Artificial
<220> FEATURE:
<223> OTHER INFORMATION: synthetic construct

<400> SEQUENCE: 91

Arg Ala Ser Glu Ser Val Asp Trp Trp Gly Asn Ser Phe Met His
1               5                   10                  15

<210> SEQ ID NO 92
<211> LENGTH: 15
<212> TYPE: PRT
<213> ORGANISM: Artificial
<220> FEATURE:
<223> OTHER INFORMATION: synthetic construct

<400> SEQUENCE: 92

Arg Ala Ser Glu Ser Val Asp Phe Tyr Gly Asn Ser Phe Met His
1               5                   10                  15

<210> SEQ ID NO 93
<211> LENGTH: 15
<212> TYPE: PRT
<213> ORGANISM: Artificial
<220> FEATURE:
<223> OTHER INFORMATION: synthetic construct

<400> SEQUENCE: 93

Arg Ala Ser Glu Ser Val Asp Trp Tyr Gly Asn Ser Phe Met His
1               5                   10                  15

<210> SEQ ID NO 94
<211> LENGTH: 7
<212> TYPE: PRT
<213> ORGANISM: Artificial
<220> FEATURE:
<223> OTHER INFORMATION: synthetic construct

<400> SEQUENCE: 94

Tyr Ala Ser Asn Leu Glu Ser
1               5

<210> SEQ ID NO 95
<211> LENGTH: 9
<212> TYPE: PRT
<213> ORGANISM: Artificial
<220> FEATURE:
<223> OTHER INFORMATION: synthetic construct

<400> SEQUENCE: 95

Gln Gln Asn Ala Glu Asp Pro Leu Thr
1               5

<210> SEQ ID NO 96
<211> LENGTH: 5
<212> TYPE: PRT
<213> ORGANISM: Artificial
<220> FEATURE:
<223> OTHER INFORMATION: synthetic construct

<400> SEQUENCE: 96

Ser Tyr Trp Met Asn
1               5

<210> SEQ ID NO 97

```
<211> LENGTH: 17
<212> TYPE: PRT
<213> ORGANISM: Artificial
<220> FEATURE:
<223> OTHER INFORMATION: synthetic construct

<400> SEQUENCE: 97

Gln Ile Phe Pro Ala Ser Gly Ser Thr Asn Tyr Gly Glu Met Phe Glu
1               5                   10                  15
Gly

<210> SEQ ID NO 98
<211> LENGTH: 12
<212> TYPE: PRT
<213> ORGANISM: Artificial
<220> FEATURE:
<223> OTHER INFORMATION: synthetic construct

<400> SEQUENCE: 98

Gly Ile Gly Asn Tyr Ala Leu Asp Ala Met Asp Tyr
1               5                   10

<210> SEQ ID NO 99
<211> LENGTH: 17
<212> TYPE: PRT
<213> ORGANISM: Artificial
<220> FEATURE:
<223> OTHER INFORMATION: synthetic construct

<400> SEQUENCE: 99

Gln Ile Phe Pro Ala Leu Gly Ser Thr Asn Tyr Gly Glu Met Phe Glu
1               5                   10                  15
Gly

<210> SEQ ID NO 100
<211> LENGTH: 5
<212> TYPE: PRT
<213> ORGANISM: Artificial
<220> FEATURE:
<223> OTHER INFORMATION: synthetic construct

<400> SEQUENCE: 100

Ser Glu Trp Met Asn
1               5

<210> SEQ ID NO 101
<211> LENGTH: 17
<212> TYPE: PRT
<213> ORGANISM: Artificial
<220> FEATURE:
<223> OTHER INFORMATION: synthetic construct

<400> SEQUENCE: 101

Gln Ile Phe Pro Ala Leu Gly Ser Thr Asn Tyr Asn Glu Met Tyr Glu
1               5                   10                  15
Gly

<210> SEQ ID NO 102
<211> LENGTH: 17
<212> TYPE: PRT
<213> ORGANISM: Artificial
<220> FEATURE:
<223> OTHER INFORMATION: synthetic construct

<400> SEQUENCE: 102
```

Gln Ile Phe Pro Phe Ser Gly Ser Thr Asn Tyr Asn Glu Met Phe Glu
1               5                   10                  15

Gly

<210> SEQ ID NO 103
<211> LENGTH: 363
<212> TYPE: PRT
<213> ORGANISM: Artificial
<220> FEATURE:
<223> OTHER INFORMATION: synthetic construct

<400> SEQUENCE: 103

Cys Ala Gly Gly Thr Thr Cys Ala Gly Cys Thr Gly Gly Thr Gly Cys
1               5                   10                  15

Ala Gly Thr Cys Thr Gly Gly Thr Gly Cys Thr Gly Ala Gly Gly Thr
            20                  25                  30

Gly Ala Ala Gly Ala Ala Gly Cys Cys Thr Gly Gly Thr Gly Cys Cys
        35                  40                  45

Thr Cys Ala Gly Thr Gly Ala Ala Gly Gly Thr Cys Thr Cys Cys Thr
50                  55                  60

Gly Cys Ala Ala Gly Gly Cys Thr Thr Cys Thr Gly Gly Thr Thr Ala
65                  70                  75                  80

Cys Ala Cys Cys Thr Thr Thr Ala Cys Cys Ala Gly Cys Thr Ala Cys
            85                  90                  95

Thr Gly Gly Ala Thr Gly Ala Ala Cys Thr Gly Gly Thr Gly Cys Gly
                100                 105                 110

Gly Thr Cys Ala Gly Gly Cys Cys Cys Cys Thr Gly Gly Thr Cys Ala
            115                 120                 125

Ala Gly Gly Thr Cys Thr Thr Gly Ala Gly Thr Gly Gly Ala Thr Gly
        130                 135                 140

Gly Gly Thr Cys Ala Gly Ala Thr Thr Thr Thr Thr Cys Cys Thr Gly
145                 150                 155                 160

Cys Ala Ala Gly Thr Gly Gly Thr Ala Gly Thr Ala Cys Thr Ala Ala
                165                 170                 175

Cys Thr Ala Cys Gly Gly Gly Gly Ala Gly Ala Thr Gly Thr Thr Cys
            180                 185                 190

Gly Ala Gly Gly Gly Cys Cys Gly Thr Gly Thr Cys Ala Cys Cys Ala
        195                 200                 205

Thr Gly Ala Cys Cys Ala Cys Ala Gly Ala Cys Ala Cys Ala Thr Cys
        210                 215                 220

Cys Ala Cys Gly Ala Gly Cys Ala Cys Ala Gly Cys Cys Thr Ala Cys
225                 230                 235                 240

Ala Thr Gly Gly Ala Gly Cys Thr Gly Cys Gly Thr Ala Gly Cys Cys
                245                 250                 255

Thr Gly Cys Gly Thr Thr Cys Thr Gly Ala Cys Gly Ala Cys Ala Cys
            260                 265                 270

Gly Gly Cys Cys Gly Thr Gly Thr Ala Thr Thr Ala Cys Thr Gly Thr
        275                 280                 285

Gly Cys Gly Cys Gly Thr Gly Gly Ala Ala Thr Ala Gly Gly Thr Ala
        290                 295                 300

Ala Cys Thr Ala Cys Gly Cys Cys Thr Gly Gly Ala Thr Gly Cys
305                 310                 315                 320

Thr Ala Thr Gly Gly Ala Cys Thr Ala Cys Thr Gly Gly Gly Gly Cys
                325                 330                 335

Cys Ala Gly Gly Gly Cys Ala Cys Cys Cys Thr Gly Gly Thr Cys Ala

```
              340                 345                 350
Cys Cys Gly Thr Cys Thr Cys Cys Thr Cys Cys
355                 360

<210> SEQ ID NO 104
<211> LENGTH: 333
<212> TYPE: PRT
<213> ORGANISM: Artificial
<220> FEATURE:
<223> OTHER INFORMATION: synthetic construct

<400> SEQUENCE: 104

Gly Ala Cys Ala Thr Cys Cys Ala Gly Ala Thr Gly Ala Cys Cys Cys
1               5                  10                  15

Ala Gly Thr Cys Thr Cys Cys Ala Thr Cys Cys Thr Cys Cys Cys Thr
            20                  25                  30

Gly Thr Cys Thr Gly Cys Ala Thr Cys Thr Gly Thr Ala Gly Gly Ala
        35                  40                  45

Gly Ala Cys Ala Gly Ala Gly Thr Cys Ala Cys Ala Thr Cys Thr Ala
    50                  55                  60

Cys Thr Thr Gly Cys Cys Gly Gly Cys Ala Ala Gly Thr Cys Gly Ala
65                  70                  75                  80

Ala Ala Gly Thr Gly Thr Thr Gly Ala Thr Thr Thr Cys Thr Gly Gly
            85                  90                  95

Gly Gly Cys Ala Ala Thr Ala Gly Thr Thr Thr Ala Thr Gly Cys
        100                 105                 110

Ala Cys Thr Gly Gly Thr Ala Thr Cys Ala Gly Cys Ala Gly Ala Ala
    115                 120                 125

Ala Cys Cys Ala Gly Gly Ala Ala Ala Gly Cys Cys Cys Cys Thr
130                 135                 140

Ala Ala Gly Cys Thr Cys Cys Thr Gly Ala Thr Cys Thr Ala Thr Cys
145                 150                 155                 160

Thr Thr Gly Cys Ala Thr Cys Cys Ala Ala Cys Cys Thr Ala Gly Ala
            165                 170                 175

Ala Thr Cys Thr Gly Gly Ala Gly Thr Cys Cys Cys Ala Thr Cys Ala
        180                 185                 190

Ala Gly Gly Thr Thr Cys Ala Gly Thr Gly Gly Cys Ala Gly Thr Gly
    195                 200                 205

Gly Ala Thr Cys Thr Gly Gly Gly Ala Cys Ala Gly Ala Thr Thr Thr
210                 215                 220

Cys Ala Cys Thr Cys Thr Cys Ala Cys Cys Ala Thr Cys Ala Gly Cys
225                 230                 235                 240

Ala Gly Thr Cys Thr Gly Cys Ala Ala Cys Cys Thr Gly Ala Ala Gly
            245                 250                 255

Ala Thr Thr Thr Thr Gly Cys Ala Ala Cys Thr Thr Ala Cys Thr Ala
        260                 265                 270

Cys Thr Gly Thr Cys Ala Gly Cys Ala Ala Ala Thr Ala Thr Ala
    275                 280                 285

Gly Ala Gly Gly Ala Thr Cys Cys Gly Cys Thr Cys Ala Cys Gly Thr
290                 295                 300

Thr Cys Gly Gly Cys Gly Gly Ala Gly Gly Ala Cys Cys Ala Ala
305                 310                 315                 320

Gly Gly Thr Gly Gly Ala Gly Ala Thr Cys Ala Ala Ala
            325                 330
```

<210> SEQ ID NO 105
<211> LENGTH: 363
<212> TYPE: PRT
<213> ORGANISM: Artificial
<220> FEATURE:
<223> OTHER INFORMATION: synthetic construct

<400> SEQUENCE: 105

```
Cys Ala Gly Gly Thr Cys Ala Gly Cys Gly Gly Thr Gly Cys
1               5                   10                  15

Ala Gly Thr Cys Thr Gly Gly Thr Gly Cys Thr Gly Ala Gly Gly Thr
            20                  25                  30

Gly Ala Ala Gly Ala Ala Gly Cys Cys Thr Gly Gly Thr Gly Cys Cys
35                  40                  45

Thr Cys Ala Gly Thr Gly Ala Ala Gly Gly Thr Cys Thr Cys Cys Thr
            50                  55                  60

Gly Cys Ala Ala Gly Gly Cys Thr Thr Cys Thr Gly Gly Thr Thr Ala
65                  70                  75                  80

Cys Ala Cys Cys Thr Thr Thr Ala Cys Cys Thr Cys Cys Thr Ala Cys
            85                  90                  95

Thr Gly Gly Ala Thr Gly Ala Ala Cys Thr Gly Gly Gly Thr Gly Cys
100                 105                 110

Gly Thr Cys Ala Gly Gly Cys Cys Cys Cys Thr Gly Gly Thr Cys Ala
115                 120                 125

Ala Gly Gly Thr Cys Thr Thr Gly Ala Gly Thr Gly Gly Ala Thr Gly
            130                 135                 140

Gly Gly Thr Cys Ala Gly Ala Thr Thr Thr Thr Thr Cys Cys Thr Gly
145                 150                 155                 160

Cys Ala Thr Thr Gly Gly Gly Thr Ala Gly Thr Ala Cys Thr Ala Ala
            165                 170                 175

Cys Thr Ala Cys Gly Gly Gly Ala Gly Ala Thr Gly Thr Thr Thr Cys
180                 185                 190

Gly Ala Gly Gly Gly Cys Cys Gly Thr Gly Thr Cys Ala Cys Cys Ala
195                 200                 205

Thr Gly Ala Cys Cys Ala Cys Ala Gly Ala Cys Ala Cys Ala Thr Cys
210                 215                 220

Cys Ala Cys Gly Ala Gly Cys Ala Cys Ala Gly Cys Cys Thr Ala Cys
            225                 230                 235                 240

Ala Thr Gly Gly Ala Gly Cys Thr Gly Cys Gly Thr Ala Gly Cys Cys
245                 250                 255

Thr Gly Cys Gly Thr Thr Cys Thr Gly Ala Cys Gly Ala Cys Ala Cys
            260                 265                 270

Gly Gly Cys Cys Gly Thr Gly Thr Ala Thr Thr Ala Cys Thr Gly Thr
275                 280                 285

Gly Cys Gly Cys Gly Thr Gly Gly Ala Ala Thr Ala Gly Gly Thr Ala
290                 295                 300

Ala Cys Thr Ala Cys Gly Cys Cys Thr Gly Gly Ala Thr Gly Cys
305                 310                 315                 320

Thr Ala Thr Gly Gly Ala Cys Thr Ala Cys Thr Gly Gly Gly Gly Cys
325                 330                 335

Cys Ala Gly Gly Gly Cys Ala Cys Cys Cys Thr Gly Gly Thr Cys Ala
            340                 345                 350

Cys Cys Gly Thr Cys Thr Cys Cys Thr Cys Ala
355                 360
```

```
<210> SEQ ID NO 106
<211> LENGTH: 333
<212> TYPE: PRT
<213> ORGANISM: Artificial
<220> FEATURE:
<223> OTHER INFORMATION: synthetic construct

<400> SEQUENCE: 106

Gly Ala Cys Ala Thr Cys Cys Ala Gly Ala Thr Gly Ala Cys Cys Cys
1               5                   10                  15

Ala Gly Thr Cys Thr Cys Cys Ala Thr Cys Cys Thr Cys Cys Cys Thr
            20                  25                  30

Gly Thr Cys Thr Gly Cys Ala Thr Cys Thr Gly Thr Ala Gly Gly Ala
        35                  40                  45

Gly Ala Cys Ala Gly Ala Gly Thr Cys Ala Cys Cys Ala Thr Cys Ala
    50                  55                  60

Cys Thr Thr Gly Cys Cys Gly Gly Cys Ala Ala Gly Thr Cys Ala
65                  70                  75                  80

Ala Ala Gly Thr Gly Thr Thr Gly Ala Thr Thr Gly Gly Thr Gly Gly
                85                  90                  95

Gly Gly Cys Ala Ala Thr Ala Gly Thr Thr Thr Ala Thr Gly Cys
            100                 105                 110

Ala Cys Thr Gly Gly Thr Ala Thr Cys Ala Gly Cys Ala Gly Ala Ala
        115                 120                 125

Ala Cys Cys Ala Gly Gly Gly Ala Ala Ala Gly Cys Cys Cys Cys Thr
    130                 135                 140

Ala Ala Gly Cys Thr Cys Cys Thr Gly Ala Thr Cys Thr Ala Thr Cys
145                 150                 155                 160

Thr Thr Gly Cys Ala Thr Cys Cys Ala Cys Cys Thr Ala Gly Ala
                165                 170                 175

Ala Thr Cys Thr Gly Gly Ala Gly Thr Cys Cys Cys Ala Thr Cys Ala
            180                 185                 190

Ala Gly Gly Thr Thr Cys Ala Gly Thr Gly Gly Cys Ala Gly Thr Gly
        195                 200                 205

Gly Ala Thr Cys Thr Gly Gly Gly Ala Cys Ala Gly Ala Thr Thr Thr
    210                 215                 220

Cys Ala Cys Thr Cys Thr Cys Ala Cys Cys Ala Thr Cys Ala Gly Cys
225                 230                 235                 240

Ala Gly Thr Cys Thr Gly Cys Ala Ala Cys Thr Gly Ala Ala Gly
                245                 250                 255

Ala Thr Thr Thr Thr Gly Cys Ala Ala Cys Thr Thr Ala Cys Thr Ala
            260                 265                 270

Cys Thr Gly Thr Cys Ala Gly Cys Ala Ala Ala Thr Ala Thr Ala
        275                 280                 285

Gly Ala Gly Gly Ala Thr Cys Cys Gly Cys Thr Cys Ala Cys Gly Thr
    290                 295                 300

Thr Cys Gly Gly Cys Gly Gly Ala Gly Gly Ala Cys Cys Ala Ala
305                 310                 315                 320

Gly Gly Thr Gly Gly Ala Gly Ala Thr Cys Ala Ala Ala
                325                 330

<210> SEQ ID NO 107
<211> LENGTH: 363
<212> TYPE: PRT
<213> ORGANISM: Artificial
<220> FEATURE:
<223> OTHER INFORMATION: synthetic construct
```

<400> SEQUENCE: 107

| Cys | Ala | Gly | Gly | Thr | Cys | Ala | Gly | Cys | Thr | Gly | Thr | Gly | Cys |
|---|---|---|---|---|---|---|---|---|---|---|---|---|---|
| 1 | | | | 5 | | | | 10 | | | | 15 | |

Ala Gly Thr Cys Thr Gly Gly Thr Gly Cys Thr Gly Ala Gly Gly Thr
20                  25                  30

Gly Ala Ala Gly Ala Ala Gly Cys Cys Thr Gly Thr Gly Cys Cys
35                  40                  45

Thr Cys Ala Gly Thr Gly Ala Ala Gly Gly Thr Cys Thr Cys Cys Thr
50                  55                  60

Gly Cys Ala Ala Gly Gly Cys Thr Thr Cys Thr Gly Gly Thr Thr Ala
65                  70                  75                  80

Cys Ala Cys Cys Thr Thr Thr Ala Cys Thr Cys Cys Gly Ala Gly
85                  90                  95

Thr Gly Gly Ala Thr Gly Ala Ala Cys Thr Gly Gly Thr Gly Cys
100                 105                 110

Gly Thr Cys Ala Gly Gly Cys Cys Cys Cys Thr Gly Gly Thr Cys Ala
115                 120                 125

Ala Gly Gly Thr Cys Thr Thr Gly Ala Gly Thr Gly Ala Thr Gly
130                 135                 140

Gly Gly Thr Cys Ala Gly Ala Thr Thr Thr Thr Cys Cys Thr Gly
145                 150                 155                 160

Cys Ala Thr Thr Gly Gly Thr Ala Gly Thr Ala Cys Thr Ala Ala
165                 170                 175

Cys Thr Ala Cys Ala Ala Thr Gly Ala Gly Ala Thr Gly Thr Ala Cys
180                 185                 190

Gly Ala Gly Gly Gly Cys Cys Gly Thr Gly Thr Cys Ala Cys Ala
195                 200                 205

Thr Gly Ala Cys Cys Ala Cys Ala Gly Ala Cys Ala Cys Ala Thr Cys
210                 215                 220

Cys Ala Cys Gly Ala Gly Cys Ala Cys Ala Gly Cys Cys Thr Ala Cys
225                 230                 235                 240

Ala Thr Gly Gly Ala Gly Cys Thr Gly Cys Gly Thr Ala Gly Cys Cys
245 250 255

Thr Gly Cys Gly Thr Thr Cys Thr Gly Ala Cys Gly Ala Cys Ala Cys
260 265 270

Gly Gly Cys Cys Gly Thr Gly Thr Ala Thr Thr Ala Cys Thr Gly Thr
275 280 285

Gly Cys Gly Cys Gly Thr Gly Gly Ala Ala Thr Ala Gly Gly Thr Ala
290 295 300

Ala Cys Thr Ala Cys Gly Cys Cys Cys Thr Gly Gly Ala Thr Gly Cys
305 310 315 320

Thr Ala Thr Gly Gly Ala Cys Thr Ala Cys Thr Gly Gly Gly Gly Cys
325 330 335

Cys Ala Gly Gly Gly Cys Ala Cys Cys Cys Thr Gly Gly Thr Cys Ala
340 345 350

Cys Cys Gly Thr Cys Thr Cys Cys Thr Cys Cys
355 360

<210> SEQ ID NO 108
<211> LENGTH: 333
<212> TYPE: PRT
<213> ORGANISM: Artificial
<220> FEATURE:
<223> OTHER INFORMATION: synthetic construct

<400> SEQUENCE: 108

Gly Ala Cys Ala Thr Cys Cys Ala Gly Ala Thr Gly Ala Cys Cys Cys
1               5                   10                  15

Ala Gly Thr Cys Thr Cys Cys Ala Thr Cys Cys Thr Cys Cys Cys Thr
            20                  25                  30

Gly Thr Cys Thr Gly Cys Ala Thr Cys Thr Gly Thr Ala Gly Gly Ala
        35                  40                  45

Gly Ala Cys Ala Gly Ala Gly Thr Cys Ala Cys Ala Thr Cys Ala
    50                  55                  60

Cys Thr Thr Gly Cys Cys Gly Gly Cys Ala Ala Gly Thr Ala Gly Ala
65                  70                  75                  80

Ala Ala Gly Thr Gly Thr Thr Gly Ala Thr Thr Thr Cys Thr Ala Thr
        85                  90                  95

Gly Gly Cys Ala Ala Thr Ala Gly Thr Thr Thr Ala Thr Gly Cys
100                 105                 110

Ala Cys Thr Gly Gly Thr Ala Thr Cys Ala Gly Cys Ala Gly Ala Ala
115 120 125

Ala Cys Cys Ala Gly Gly Gly Ala Ala Ala Gly Cys Cys Cys Cys Thr
130 135 140

Ala Ala Gly Cys Thr Cys Cys Thr Gly Ala Thr Cys Thr Ala Thr Cys
145 150 155 160

Thr Thr Gly Cys Ala Thr Cys Cys Ala Ala Cys Cys Thr Ala Gly Ala
165 170 175

Ala Thr Cys Thr Gly Gly Ala Gly Thr Cys Cys Cys Ala Thr Cys Ala
180 185 190

Ala Gly Gly Thr Thr Cys Ala Gly Thr Gly Gly Cys Ala Gly Thr Gly
195 200 205

Gly Ala Thr Cys Thr Gly Gly Gly Ala Cys Ala Gly Ala Thr Thr Thr
210 215 220

Cys Ala Cys Thr Cys Thr Cys Ala Cys Cys Ala Thr Cys Ala Gly Cys
225 230 235 240

Ala Gly Thr Cys Thr Gly Cys Ala Ala Cys Cys Thr Gly Ala Ala Gly
245 250 255

Ala Thr Thr Thr Thr Gly Cys Ala Ala Cys Thr Thr Ala Cys Thr Ala
260 265 270

Cys Thr Gly Thr Cys Ala Gly Cys Ala Ala Ala Ala Thr Ala Thr Ala
275 280 285

Gly Ala Gly Gly Ala Thr Cys Cys Gly Cys Thr Cys Ala Cys Gly Thr
290 295 300

Thr Cys Gly Gly Cys Gly Gly Ala Gly Gly Gly Ala Cys Cys Ala Ala
305 310 315 320

Gly Gly Thr Gly Gly Ala Gly Ala Thr Cys Ala Ala Ala
325 330

<210> SEQ ID NO 109
<211> LENGTH: 363
<212> TYPE: PRT
<213> ORGANISM: Artificial
<220> FEATURE:
<223> OTHER INFORMATION: synthetic construct

<400> SEQUENCE: 109

Cys Ala Gly Gly Thr Thr Cys Ala Gly Cys Thr Gly Gly Thr Gly Cys
1 5 10 15

```
Ala Gly Thr Cys Thr Gly Gly Thr Gly Cys Thr Gly Ala Gly Gly Thr
 20                  25                  30

Gly Ala Ala Gly Ala Ala Gly Cys Cys Thr Gly Gly Thr Gly Cys Cys
 35                  40                  45

Thr Cys Ala Gly Thr Gly Ala Ala Gly Gly Thr Cys Thr Cys Cys Thr
 50                  55                  60

Gly Cys Ala Ala Gly Gly Cys Thr Thr Cys Thr Gly Gly Thr Thr Ala
 65                  70                  75                  80

Cys Ala Cys Cys Thr Thr Thr Ala Cys Thr Cys Cys Thr Ala Cys
 85                  90                  95

Thr Gly Gly Ala Thr Gly Ala Ala Cys Thr Gly Gly Thr Gly Cys
100                 105                 110

Gly Thr Cys Ala Gly Gly Cys Cys Cys Thr Gly Gly Thr Cys Ala
115                 120                 125

Ala Gly Gly Thr Cys Thr Thr Gly Ala Gly Thr Gly Gly Ala Thr Gly
130                 135                 140

Gly Gly Thr Cys Ala Gly

```
Ala Gly Thr Cys Thr Cys Ala Thr Cys Thr Cys Cys Thr
 20                  25                  30

Gly Thr Cys Thr Gly Cys Ala Thr Cys Thr Gly Ala Gly Gly Ala
 35                  40                  45

Gly Ala Cys Ala Gly Ala Gly Thr Cys Ala Cys Cys Ala Thr Cys Ala
 50                  55                  60

Cys Thr Thr Gly Cys Cys Gly Gly Cys Ala Ala Gly Thr Gly Ala
 65                  70                  75                  80

Ala Ala Gly Thr Gly Thr Thr Gly Ala Thr Thr Gly Gly Thr Ala Thr
 85                  90                  95

Gly Gly Cys Ala Ala Thr Ala Gly Thr Thr Thr Ala Thr Gly Cys
100                 105                 110

Ala Cys Thr Gly Gly Thr Ala Thr Cys Ala Gly Cys Ala Gly Ala Ala
115                 120                 125

```
Thr Cys Ala Gly Thr Gly Ala Ala Gly Gly Thr Cys Thr Cys Cys Thr
 50                  55                  60

Gly Cys Ala Ala Gly Gly Cys Thr Thr Cys Thr Gly Gly Thr Thr Ala
 65                  70                  75                  80

Cys Ala Cys Cys Thr Thr Ala Cys Thr Cys Cys Thr Ala Cys
 85                  90                  95

Thr Gly Gly Ala Thr Gly Ala Ala Cys Thr Gly Gly Thr Gly Cys
100                 105                 110

Gly Thr Cys Ala Gly Gly Cys Cys Cys Thr Gly Gly Thr Cys Ala
115                 120                 125

Ala Gly Gly Thr Cys Thr Thr Gly Ala Gly Thr Gly Gly Ala Thr Gly
130                 135                 140

Gly Gly Thr Cys Ala Gly Ala Thr Thr Thr Thr

-continued

```
Gly Ala Cys Ala Gly Ala Gly Thr Cys Ala Cys Cys Ala Thr Cys Ala
50              55                  60
Cys Thr Thr Gly Cys Cys Gly Gly Gly Cys Ala Ala Gly Thr Gly Ala
65              70                  75                          80
Ala Ala Gly Thr Gly Thr Thr Gly Ala Thr Thr Thr Cys Thr Gly Gly
85              90                  95
Gly Gly Cys Ala Ala Thr Ala Gly Thr Thr Thr Ala Thr Gly Cys
100             105                 110
Ala Cys Thr Gly Gly Thr Ala Thr Cys Ala Gly Cys Ala Gly Ala Ala
115             120                 125
Ala Cys Cys Ala Gly Gly Gly Ala Ala Ala Gly Cys Cys Cys Cys Thr
130             135                 140
Ala Ala Gly Cys Thr Cys Cys Thr Gly Ala Thr Cys Thr Ala Thr Cys
145             150                 155                         160
Thr Thr Gly Cys Ala Thr Cys Cys Ala Ala Cys Cys Thr Ala Gly Ala
165             170                 175
Ala Thr Cys Thr Gly Gly Ala Gly Thr Cys Cys Cys Ala Thr Cys Ala
180             185                 190
Ala Gly Gly Thr Thr Cys Ala Gly Thr Gly Gly Cys Ala Gly Thr Gly
195             200                 205
Gly Ala Thr Cys Thr Gly Gly Gly Ala Cys Ala Gly Ala Thr Thr Thr
210             215                 220
Cys Ala Cys Thr Cys Thr Cys Ala Cys Cys Ala Thr Cys Ala Gly Cys
225             230                 235                         240
Ala Gly Thr Cys Thr Gly Cys Ala Ala Cys Cys Thr Gly Ala Ala Gly
245             250                 255
Ala Thr Thr Thr Thr Gly Cys Ala Ala Cys Thr Thr Ala Cys Thr Ala
260             265                 270
Cys Thr Gly Thr Cys Ala Gly Cys Ala Ala Ala Thr Gly Cys Cys
275             280                 285
Gly Ala Gly Gly Ala Thr Cys Cys Gly Cys Thr Cys Ala Cys Gly Thr
290             295                 300
Thr Cys Gly Gly Cys Gly Gly Ala Gly Gly Gly Ala Cys Cys Ala Ala
305             310                 315                         320
Gly Gly Thr Gly Gly Ala Gly Ala Thr Cys Ala Ala Ala
325             330
```

TGF-β BINDING ANTIBODIES

CROSS REFERENCE TO RELATED APPLICATIONS

This application is a national-stage application of International Application No. PCT/US06/62397, filed Dec. 20, 2006, which claims benefit of U.S. Provisional Application No. 60/753,956, filed Dec. 23, 2005.

FIELD OF THE INVENTION

The invention relates to treatment of cell proliferative diseases, disorders, and conditions associated with TGF-β. In particular, the invention provides antibodies and antigen-binding fragments thereof that neutralize mature, human TGF-β1, -β2, and -β3.

BACKGROUND OF THE INVENTION

The TGF-β protein family consists of three distinct isoforms (TGF-β1, -β2, and -β3) whose pathways activate and regulate multiple gene responses that influence disease states such as, e.g., cell proliferative, inflammatory, and cardiovascular conditions. TGF-β isoform expression in cancer is complex and variable with different combinations of TGF-β isoforms having different roles in particular cancers. For example, TGF-β1 and -β3 play a greater role in ovarian cancer and its progression than TGF-β2; while TGF-β1 and -β2 expression is greater in higher grade chondrosarcoma tumors than -β3. In human breast cancer, TGF-β1 and -β3 are highly expressed, with -β3 expression correlating with overall survival—patients with node metastasis and positive TGF-β3 expression have poor prognostic outcomes. However, in colon cancer, TGF-β1 and -β2 are more highly expressed than -β3 and are present at greater circulating levels than in cancer-free individuals. In glioma cancer, TGF-β2 is pivotal for cell migration. Consequently, there is a need to modulate multiple TGF-β isoform expression in cell proliferation conditions such as cancer.

U.S. Pat. No. 5,571,714 discloses the use of anti-TGF antibodies in treating malignancies and metastatic cancer, and in particular, discloses a murine antibody designated 1D11.16 (ATCC No. HB9849) that is said to bind both TGF-β1 and -β2. This document states that antibody 1D11.16 binds TGF-β2 with a Ka of merely $3.4 \times 10^8$ L/mol (Kd=1/Ka).

The treatment of cell proliferative disorders, such as malignancies and cancers, may be improved by use of antibodies that neutralize mature, human, TGF-β1, -β2, and -β3 with improved binding kinetics and affinity. Substantial physical and chemical stability, adequate pharmacokinetics, and good solubility are also desirable for a pharmaceutical product. Consequently, an unmet need remains for antibodies having characteristics suitable for the pharmaceutical treatment of cell proliferative disorders.

SUMMARY OF THE INVENTION

The present invention provides monoclonal antibody compositions that neutralize mature human TGF-β1, -β2 and -β3 with a $K_d$ less than 4 pM for mature human TGF-β1, and a $K_d$ less than 8 pM for mature human TGF-β2, and a $K_d$ less than 4 pM for mature human TGF-β3. The invention also provides antibodies having the following combinations of light chain- (LCVR) and heavy chain-variable region (HCVR) sequences: SEQ ID NO: 27 and 51, 27 and 59, 27 and 60, 27 and 61, 27 and 62, 27 and 63, 27 and 64, 28 and 52, 29 and 51, 30 and 53, 31 and 54, 32 and 55, 33 and 56, 34 and 51, 34 and 57, 35 and 58, 36 and 51, 36 and 69, 36 and 75, 37 and 51, 38 and 51, 39 and 51, 40 and 51, 41 and 64, 41 and 67, 42 and 66, 43 and 68, 44 and 66, 45 and 51, 45 and 69, 46 and 70, 46 and 71, 47 and 71, 48 and 72, 49 and 73, 50 and 65, or 50 and 74. The invention also includes antigen-binding fragments of such antibodies, as well as antibodies and fragments having human or humanized frameworks and constant regions. The antibodies and fragments of the invention are useful to treat cell proliferative diseases, disorders, and conditions.

In one embodiment, antibodies of the present invention neutralize mature human TGF-β1, mature human TGF-β2, and mature human TGF-β3, and have an $IC_{50}$ of less than or equal to about 100 pM for mature human TGF-β1, and an $IC_{50}$ of less than or equal to about 400 pM for mature human TGF-β2, and an $IC_{50}$ of less than or equal to about 200 pM for mature human TGF-β3 in an in vitro HT-2 Cell neutralization assay.

In one embodiment, antibodies of the present invention comprises a heavy chain variable region (HCVR) and a light chain variable region (LCVR), wherein said HCVR comprises a peptide at CDRH1 with a sequence as shown in SEQ ID NO: 96 or SEQ ID NO: 100, a peptide at CDRH2 with a sequence as shown in SEQ ID NO: 97, SEQ ID NO: 99, SEQ ID NO: 101, or SEQ ID NO: 102, and a peptide at CDRH3 with a sequence as shown in SEQ ID NO: 98, and wherein said LCVR comprises a peptide at CDRL1 with a sequence as shown in SEQ ID NO: 88, SEQ ID NO: 91, SEQ ID NO: 92, or SEQ ID NO: 93, a peptide at CDRL2 with a sequence as shown in SEQ ID NO: 89 or SEQ ID NO: 94, and a peptide at CDRL3 with a sequence as shown in SEQ ID NO: 90, or SEQ ID NO: 95.

In one embodiment, antibodies of the present invention further comprise a human framework region.

In another embodiment, antibodies of the present invention comprise a HCVR with a sequence selected from the group consisting of SEQ ID NO: 64, 68, 69, 70, and 74, and a LCVR with a sequence selected from the group consisting of SEQ ID NO: 41, 43, 45, 46, and 50.

In another embodiment, antibodies of the present invention comprise a HCVR with a sequence as shown in SEQ ID NO: 69, and a LCVR with a sequence as shown in SEQ ID NO: 45.

In one embodiment, antibodies of the present invention comprise a heavy chain with a sequence selected from the group consisting of SEQ ID NO: 77, 79, 81, 83 and 85, and a light chain with a sequence selected from the group consisting of SEQ ID NO: 76, 78, 80, 82, and 84.

In one embodiment, antibodies of the present invention comprise a heavy chain with a sequence as shown in SEQ ID NO: 81 and a light chain with a sequence as shown in SEQ ID NO: 80.

The invention provides a method of treating cell proliferative disorders in a mammal, preferably a primate, and more preferably a human, comprising administering to a mammal in need of such treatment an effective amount of an antibody of the invention or a fragment thereof.

The invention provides a method of treating a disease or condition in which fibrogenesis and/or angiogenesis mediated by TGF-β are implicated in a mammal, preferably a primate, and more preferably a human, including myelodysplastic syndrome (MDS)/myeloproliferative disorder (MPD), breast cancer, prostate cancer, ovarian cancer, hepatocellular carcinoma, pancreatic cancer, multiple myeloma, colorectal cancer, other hematological malignancies (hairy cell leukemia, CML, AML, etc), comprising administering to a mammal in need of such treatment an effective amount of an antibody of the invention or a fragment thereof. This may further comprise administering to the mammal an effective amount of a therapeutic agent other than anti-TGF-β antibodies, such as a chemotherapeutic agent, anti-angiogenic agent, or cytotoxic chemotherapy.

In another embodiment, this invention provides a method of treating a patient with HER2-overexpressing metastatic breast cancer, comprising administering to the patent an effective amount of an antibody of the invention and an antibody that blocks signaling through the HER-2 receptor, i.e. trastuzumab.

The present invention also provides a pharmaceutical composition comprising an antibody of the invention in combination with a pharmaceutically acceptable carrier, diluent or excipient.

This invention also provides the use of an antibody of the invention for the manufacture of a medicament for treating cell proliferative disorders in mammals. Additionally, this invention provides a pharmaceutical composition adapted for treating cell proliferative disorders comprising an antibody of the invention in combination with one or more pharmaceutically acceptable excipients, carriers, or diluents thereof. The invention also provides the use of an antibody of the invention for the manufacture of a medicament for treating a disease or condition capable of being improved or prevented by neutralizing TGF-β activities.

This invention also provides the use of an antibody of the invention for the manufacture of a medicament for the treatment of a disease or condition in which fibrogenesis and/or angiogenesis mediated by TGF-β are implicated in a mammal, preferably a primate, and more preferably a human, including MDS/MPD, breast cancer, prostate cancer, ovarian cancer, hepatocellular carcinoma, pancreatic cancer, multiple myeloma, colorectal cancer, other hematological malignancies (hairy cell leukemia, CML, AML, etc), comprising administering to a mammal in need of such treatment an effective amount of an antibody of the invention or a fragment thereof. This may further comprise administering to the mammal an effective amount of a therapeutic agent other than anti-TGF-β antibodies, such as a chemotherapeutic, anti-angiogenic, or cytotoxic agent, or a cytokine. Furthermore, this invention provides a pharmaceutical composition adapted for the treatment of conditions in which neutralization or reduction of TGF-β activities would be beneficial in a mammal, including MDS/MPD, breast cancer, prostate cancer, ovarian cancer, hepatocellular carcinoma, pancreatic cancer, multiple myeloma, colorectal cancer, other hematological malignancies (hairy cell leukemia, CML, AML, etc), comprising an antibody of the invention in combination with one or more pharmaceutically acceptable excipients, carriers, or diluents. The invention also provides the use of an antibody of the invention for the manufacture of a medicament for treating a disease or condition capable of being improved or prevented by neutralizing or reducing TGF-β activities.

BRIEF DESCRIPTION OF THE DRAWINGS

FIGS. 1A and B show the amino acid sequences of the heavy chain and light chain variable regions of preferred antibodies of the invention respectively. The CDR domains are in bold print.

FIGS. 2A and B shows the alignment of the amino acid sequence of the CDR domains of preferred antibodies of the present invention. The variations are in bold print and underlined.

FIG. 3 lists the amino acid sequences of the light chain and heavy chain of a monoclonal antibody of the invention, i.e., mAb 12.7.

DETAILED DESCRIPTION OF THE INVENTION

The term a "monoclonal antibody" refers to a composition with a homogeneous antibody population, comprising of four peptide chains, two heavy (H) chains and two light (L) chains interconnected by disulfide bonds. The amino terminal portion of each chain includes a variable region of about 100-110 or more amino acids. This variable region of each chain includes three complementary determining regions (CDRs) that recognizes and binds a particular antigen. A "monoclonal antibody" can be an intact antibody (comprising a complete light chain and a complete heavy chain), a substantially intact antibody, or a portion or fragment of an antibody comprising an antigen-binding portion, e.g., a Fab fragment, or F(ab')$_2$ fragment of an antibody. Moreover, a "monoclonal antibody" can be a single-chain variable fragment (scFv), consisting of the variable heavy chain region (VH) and the variable light chain region (VL) of an antibody joined together by a flexible peptide linker.

A "homogeneous antibody population" refers to a homogeneous or substantially homogeneous antibody population (i.e., at least about 85%, 87%, 90%, 91%, 92%, 93%, 94%, 95%, 96%, more preferably at least about 97% or 98% or most preferably at least 99% of the antibodies in the population would compete in an ELISA assay for the same antigen or epitope). Antibodies may or may not be glycosylated and still fall within the bounds of the invention. Monoclonal antibodies may be homogeneous if they have identical amino acid sequence although they may differ in a post-translational modification, e.g., glycosylation pattern.

The term "effective amount" is taken to mean a dose of a compound of Formula I necessary to achieve the desired pharmacological effect.

The term "epitope" refers to that portion of a molecule capable of being recognized by and bound by an antibody at one or more of the antibody's antigen-binding regions. Epitopes often consist of a chemically active surface grouping of molecules such as amino acids or sugar side chains and have specific three-dimensional structural characteristics as well as specific charge characteristics.

The term "Kd" refers to the dissociation constant of a particular antibody-antigen interaction. It is calculated by the formula: $k_{off}/K_{on}$=Kd. The term "$k_{on}$" refers to the association or on rate constant, or specific reaction rate, of the forward, or complex-forming, reaction, measured in units: M-1sec-1. The term "$k_{off}$" refers to the dissociation or off rate constant, or specific reaction rate, for dissociation of an antibody from the antibody/antigen complex, measured in units: 1/second. The affinity of a monoclonal antibody of the present invention is often correlated with a lower $k_{off}$ more so than a higher $k_{on}$, however, not being bound by theory, both improved $k_{off}$ and $k_{on}$, embodiments are encompassed. In a more preferred embodiment, monoclonal antibodies of the present invention are high potency antibodies or fragments thereof, generally exhibiting low $k_{off}$ values.

The term "neutralize" as used herein with respect to an activity of a monoclonal antibody of the invention means the ability to substantially antagonize, prohibit, prevent, restrain, slow, disrupt, eliminate, stop, reduce or reverse e.g., progression or severity of that which is being inhibited including, but not limited to, a biological activity or property, a disease or a condition. The inhibition or neutralization is preferably at least about 10%, 20%, 30%, 40%, 50%, 60%, 70%, 80%, 90%, 95% or higher.

With respect to the binding and neutralization capabilities of antibodies of the invention, the TGF-β referred to herein is the mature, human, biologically active form of TGF-β1, TGF-β2, and TGF-β3 (SEQ ID NO: 1, 2, and 3). See also, e.g., NCBI accession No: P01137, NP_003229, and NP_003230 describing DNA and amino acid sequences of, respectively, human TGF-β1, -β2, and -β3 (including their precursor domains and mature portions). A mature disulfide-linked homodimeric human TGF-β1, -β2, or -β3 contains two 112 amino acid residue polypeptides and has a predicted molecular mass of approximately 25 kDa. Antibodies of the invention bind and neutralize such mature TGF-β3 isoforms but do not show significant binding of latent TGF-β1, -β2, and -β3 isoforms under similar conditions.

Affinity and binding kinetic improvements solve antibody problems, for example, by helping to increase pharmacokinetic and safety profiles; by reducing dosing, toxicity, and cost of therapy; and by improving biological efficacy. The dissociation constant ($K_d$) of an antibody may be found using art methods, for example, Kinexa® (see, e.g., Darling, et al., 2004 ASSAY and Drug Development Technologies 2:647-57) or BIAcore® AB (Upsala, Sweden), or adapting Karlsson et al., 1991 J. Immunol. Methods 145, 299-340. The term "$k_{on}$" herein refers to the association or on-rate constant, or specific reaction rate, of the forward, or antibody:antigen complex-forming reaction, $M^{-1}sec^{-1}$. The term "$k_{off}$" herein, refers to the dissociation or "off-rate" constant, or specific reaction rate, for dissociation of an antibody from an antibody:antigen complex, ($sec^{-1}$). The term "$K_d$" herein, refers to the dissociation constant of a particular antibody:antigen complex—calculated as $K_d=k_{off}/k_{on}$. $K_a$ is the inverse of $K_d$.

The $K_d$ of an invention antibody for mature human TGF-β1 is in the range of about 0.0001 pM to about 5.0 pM. More preferably, it is in the range of about 0.001 pM to about 3.0 pM. Most preferably, it is in the range of about 0.01 pM to about 0.5 pM. The $K_d$ of an invention antibody for mature human TGF-β2 is in the range of about 0.01 pM to about 5.0 pM. More preferably, in the range of about 0.05 pM to about 2.0 pM, and most preferably, it is in the range of about 0.1 pM to about 1.5 pM. The $K_d$ of an invention antibody for mature human TGF-β3 is in the range of about 0.005 pM to about 3 pM. More preferably, it is in the range of about 0.05 pM to about 2.8 pM. Most preferably, it is in the range of about 0.2 pM to about 2 pM. Preferably the antibodies of the invention are characterized by a $K_d$ of $4.0\times10^{-12}$M or less formature human TGF-β1, a $K_d$ of $8.0\times10^{-12}$M or less for mature human TGF-β2, and a $K_d$ of $4.0\times10^{-12}$M or less for mature human TGF-β3.

The $K_d$ of an invention antibody for TGF-β1 is at least 2 fold greater than the $K_d$ of 1D11.16 for TGF-β1, more preferably is at least 25 fold greater, and most preferably is at least 50 fold greater. To be clear, greater affinity would mean a smaller $K_d$ value. The $K_d$ of an invention antibody for TGF-β2 is at least 1.5 fold greater than the $K_d$ of 1D11.16 for TGF-β2, more preferably is at least 10 fold greater, and most preferably is at least 20 fold greater. The $K_d$ of an invention antibody for TGF-β3 is at least 4 fold greater than the $K_d$ of 1D11.16 for TGF-β3, more preferably is at least 6 fold greater, and most preferably is at least 10 fold greater.

The $K_d$ of an invention Fab for TGF-β1 is in the range of about 0.009 pM to about 75.0 pM, is more preferably in the range of about 0.018 pM to about 50 pM, and is most preferably in the range of about 0.02 pM to about 25 pM. The $K_d$ of an invention Fab for mature human TGF-β2 is in the range of about 0.0045 pM to about 60 pM, is more preferably in the range of about 0.002 pM to about 45 pM, and is most preferably in the range of about 0.02 pM to about 35 pM. The $K_d$ of an invention Fab for TGF-β1 is at least 30 fold greater than the $K_d$ of 1D11.16 for TGF-β1, more preferably is at least 300 fold greater, and most preferably is at least 1500 fold greater. The $K_d$ of an invention Fab for TGF-β2 is at least 10 fold greater than the $K_d$ of 1D11.16 for TGF-β2, more preferably is at least 100 fold greater, and most preferably is at least 500 fold greater.

Invention antibodies exhibit $k_{off}$ for mature human TGF-β1 preferably in the range of about 110 to about 1 (all values for $k_{off}$ are $\times10^{-6}s^{-1}$), more preferably in the range of about 50 to about 6, and even more preferably in the range of about 15 to about 4; for mature human TGF-β2 preferably in the range of about 240 to about 1, more preferably in the range of about 50 to about 2, and even more preferably in the range of about 20 to about 4; and for mature human TGF-β3 preferably in the range of about 90 to about 1, more preferably in the range of about 50 to about 4, and even more preferably in the range of about 35 to about 6.

Invention antibodies exhibit $k_{off}$ improvement over 1D11.16 for TGF-β1, -β2, and -β3 in the range of about 2 to about 50 fold, more preferably in the range of about 2.5 to about 25 fold, and even more preferably in the range of about 3 to about 15 fold.

In another embodiment, an invention antibody has a $k_{on}$ greater than 5 for mature human TGF-β1, greater than 2.8 for mature human TGF-β2, and greater than 1.56 for mature human TGF-β3 (all values for $k_{on}$ are $\times10^7 M^{-1} s^{-1}$). The $k_{on}$ for mature human TGF-β11 is preferably in the range of about 1.5 to about 60, more preferably in the range of about 2 to about 45, and even more preferably in the range of about 3 to about 30; for mature human TGF-β2 is preferably in the range of about 1 to about 40, more preferably in the range of about 1 to about 25, and even more preferably in the range of about 1 to about 15; and for mature human TGF-β3 is preferably in the range of about 1.2 to about 20, more preferably in the range of about 1.2 to about 10, and even more preferably in the range of about 1.2 to about 5. Invention antibodies exhibit an average $k_{on}$ improvement over 1-D11.16 for TGF-β1, -β2, and -β3 preferably in the range of about 1.5 to about 40 fold, more preferably in the range of about 2 to about 15 fold, and even more preferably in the range of about 2 to about 10 fold. In a preferred embodiment, an invention antibody binds TGF-β1 over TGF-β2 and β3.

An antibody is said to "neutralize" its antigen if antibody binding to the antigen results in complete or partial, inhibition or reduction, of a biological function of the antigen. Neutralization of a TGF-β isoform's biological activity is assessed by measuring the complete or partial, inhibition or reduction, of one or more in vitro or in vivo indicators of TGF-β activity such as, receptor binding, an inhibitory effect on cell growth; chemotaxis, apoptosis, intracellular protein phosphorylation, or signal transduction. Most preferably, the ability to neutralize TGF-β activity is assessed, as described herein, by an HT-2 cell proliferation assay or by measuring the inhibition of Smad2 phosphorylation.

Antibodies of the invention neutralize mature human TGF-β1, mature human TGF-β2, and mature human TGF-β3, and have an $IC_{50}$ of less than or equal to about 100 pM, 75 pM, 50 pM, 25 pM, 17.5 pM, 10 pM, 4 pM, or 3 pM for mature human TGF-β1, an $IC_{50}$ of less than or equal to about 400 pM, 345 pM, 200 pM, 100 pM, 77.5 pM, 50 pM, 40 pM, or 23 pM for mature human TGF-β2, and an $IC_{50}$ of less than or equal to about 200 pM, 115 pM, 105 pM, 75 pM, 50 pM, 45 pM, or 35 pM for mature human TGF-β3 in an in vitro HT-2 Cell neutralization assay.

Improved neutralizing activity increases pharmacokinetic and safety profiles; reduces dosing, toxicity, and cost of therapy; and improves biological efficacy. In a preferred embodiment, the $IC_{50}$ of an invention antibody in the HT-2 cell proliferation/neutralization assay as described herein is less than about 20 pM for TGF-β1, less than about 325 pM for TGF-β2, and less than about 125 pM for TGF-β3. Against TGF-β1, an invention antibody preferably has an $IC_{50}$ in the range of about 0.1 to about 50 pM, more preferably in the range of about 0.1 to about 30 pM, and most preferably in the range of about 0.1 to about 20 pM. Against TGF-β2, an invention antibody preferably has an $IC_{50}$ in the range of about 1 to about 400 pM, more preferably in the range of about 10 to about 350 pM, and most preferably in the range of about 15 to about 325 pM. Against TGF-β3, an invention antibody preferably has an $IC_{50}$ in the range of about 0.1 to about 200 pM, more preferably in the range of about 1 to about 150 pM, and most preferably in the range of about 10 to about 125 pM.

In another embodiment, invention antibodies exhibit on average an improvement of $IC_{50}$ over 1D11.16 in an HT-2 cell proliferation assay for TGF-β1 in the range of about 100 to about 600 fold, more preferably in the range of about 200 to about 500 fold, and even more preferably in the range of about 300 to about 400 fold; for TGF-β2 in the range of about 10 to about 400 fold, more preferably in the range of about 25 to about 300 fold, and even more preferably in the range of about 50 to about 200; and for TGF-β3 in the range of about 2 to about 200 fold, more preferably in the range of about 4 to about 50 fold, and even more preferably in the range of about 6 to about 25.

The concentration of an antibody required to neutralize a TGF-β activity is dependent on various parameters, such as, e.g., cytokine concentration, cell type, growth conditions, and type of activity studied. The neutralization character of an invention antibody is assessed by measuring the degree of inhibition of the phosphorylation of Smad2 protein in an U87MG human tumor xenograft model assay, as described herein. In another preferred embodiment, an invention antibody has a $TED_{50}$ (therapeutic effective dose) in such an assay in the range of about 100 to about 200 mg/kg, more preferably in the range of about 50 to about 80 mg/kg; and even more preferably in the range of about 5 to about 25 mg/kg. Certain antibodies and fragments of the invention have specific CDRs: VHCDR1 $X_1X_2$WMN [SEQ ID NO:10, where $X_1$ is either T or S; and $X_2$ is either E, or Y]; VHCDR2 QIFP$X_1X_2$GSTNY$X_3$EM$X_4$EG [SEQ ID NO:11, where $X_1$ is either A, or F; $X_2$ is either S, T, or L; $X_3$ is either N, G, S, D, or A; $X_4$ is either F, or Y]; VHCDR3G$X_1$GNYALDAMDY [SEQ ID NO:12, where $X_1$ is either D, I, M, Y, L, V, Q, or F]; VLCDR1RASESVD$X_1X_2$GNSFMH [SEQ ID NO:13, where $X_1$ is either S, Y, F, or L; $X_2$ is either Y or W]; VLCDR2 $X_1$ASNLES [SEQ ID NO:14, where $X_1$ is either L, or Y]; and VLCDR3 $X_1$Q$X_2X_3$EDPLT [SEQ ID NO: 15, where $X_1$ is either Q, T, or C; $X_2$ is either N, or H; $X_3$ is either N, I, M, D, T, or A].

Further encompassed are antibodies created with CDRs from such formulae after engineering the CDRs (in appropriate orientation) in human or humanized antibody framework sequences to produce invention compositions that neutralize mature, human TGF-β1, -β2, and -β3. Any art-known method may be used to incorporate specific CDRs within framework sequences. As described, variable human or humanized framework sequences can be derived from any germline or rearranged human variable domain, or, e.g., synthetic variable domain based on consensus sequences of known human variable domains. Preferred variable domain framework sequences are those that do not significantly affect the biological properties of an anti-TGF-β1, -β2, and -β3 antibody embodiment—that is, the ability to bind with high affinity and neutralize mature human TGF-β1, -β2, and -β3. Preferably, such frameworks additionally do not elicit significant immunogenic reactions when administered to a human. Framework sequences can be sequences of naturally occurring human antibodies or consensus sequences of several human antibodies.

Non-limiting examples of framework sequences for the heavy chain variable region of antibody embodiments of the invention include the VH segment DP-5 (Tomlinson, et al. 1992 *J. Mol. Biol.* 227:776-98) and the J segment JH4, JH1 or JH5 (Ravetch, et al. 1981 *Cell* 27:583-91). The Vk segment L1 (Cox, et al. 1994 *Eur. J. Immunol.* 24:827-36) and the J segment Jk4 (Hieter, et al. 1982 *J. Biol. Chem.* 10:1516-22) are non-limiting example framework sequences for the light chain variable region.

In a preferred embodiment, the HCVR FR1 framework comprises [SEQ ID NO: 16]; the HCVR FR2 framework comprises [SEQ ID NO:17]; the HCVR FR3 framework comprises [SEQ ID NO:18]; and the HCVR FR4 framework comprises [SEQ ID NO:19]. In another preferred embodiment, the LCVR FR1 framework comprises [SEQ ID NO:20]; the LCVR FR2 framework comprises [SEQ ID NO:21], the LCVR FR3 framework comprises [SEQ ID NO:22]; and the LCVR FR4 framework comprises [SEQ ID NO:23]. In another preferred embodiment, a HCVR framework comprises [SEQ ID NO: 86] wherein $X_1$ is either S, Y, F, or L; $X_2$ is either Y or W; $X_3$ is either A, or F; $X_4$ is either S, T, or L; $X_5$ is either N, G, S, D, or A; $X_5$ is either F, or Y; and $X_7$ is either D, I, M, Y, L, V, Q, or F. In another preferred embodiment, a LCVR framework comprises [SEQ ID NO: 87] wherein $X_1$ is either T or S; $X_2$ is either E, or Y; $X_3$ is either is either L, or Y; $X_4$ is either Q, T, or C; Xs is either N, or H; and $X_6$ is either N, I, M, D, T, or A.

In another preferred embodiment, framework and constant regions may contain alterations, deletions, additions, substitutions, or any combination thereof as compared with human sequences. Frameworks and constant regions in which 1, 2, 3, 4, 5, 6, 7, 8, 9, or 10 amino acids are substituted, deleted, or added in any combination are preferred. In another embodiment, the framework has 85-99% sequence identity to a disclosed framework herein.

In one embodiment, a preferred heavy chain constant region for use with an antibody binding composition of the invention is an IgG constant region. In a more preferred embodiment, the IgG constant region is an IgG1 constant region or an IgG4 constant region (even more preferably are constant regions of [SEQ ID NO:24]; or [SEQ ID NO:25]). A preferred light chain constant region sequence of the invention is [SEQ ID NO:26]. In another preferred embodiment, antibody, binding compositions contain the IgG1 Heavy chain constant region or the IgG4 Heavy chain constant region and the kappa Light chain constant region.

Also encompassed are polynucleotide sequences encoding invention antibodies. When engineering antibodies using invention CDRs, identification of residues within antibody frameworks likely to influence antigen binding donor and acceptor sequences may be determined by aligning to sequence templates derived from antibody repertoires. "Invariant residues" (Kabat et al., 1991) and "key residues" (Chothia et al., 1989) may be identified, and canonical-class assignments of the donor antigen binding loops L1-L3, H1 and H2, respectively, may be determined by screening a proposed sequence against sequence templates (see, e.g., Martin & Thornton, 1996 Mol. Biol. 263:800-15). Residues at the VH/VL interface (Chothia et al., 1985) and residues known to be structurally conserved at core sites (Chothia et al., 1998) are compared with corresponding donor and acceptor residues. Non-matching donor and acceptor framework residues at these sites are analyzed based on information from other antibodies of known structure (Berman, et al., 2000 Nucl. Acids Res. 28(1):235-42). Selection of human frameworks as templates for humanization of non-human V regions can define subsequent decisions regarding which residues to humanize. Choosing homologous templates from antibodies with known crystal structure, from germline, non-germline, or consensus sequences derived from available data bases can be employed (see, e.g., Routledge et al. (Routledge, et al., 1993 in Protein Engineering of Antibody Molecules for Prophylactic and Therapeutic Applications in Man (Clark, M., ed) pp 14-44, Academic Titles, Nottingham, UK; and B. Lo, 2004 *Antibody Engineering Methods and Protocols*, Humana Press)). Another way to engineer antibodies is to choose the closest human germline sequence as the framework to receive donor CDRs (Tomlinson et al., 1992) using a best-fit strategy to search germline sequences in databases. The germline framework method is useful because human germine sequence does not present somatic hypermutations, which are potentially immunogenic. Nucleic acid molecules encoding variant invention antibodies of a combination of framework regions and invention CDRs embedded into modified human frameworks can be engineered using a consensus human germline strategy where a human subgroup is used as the framework (see, e.g., Presta et al., 1993 J. Immunol. 151:2623-32; Couto et al., 1994 Hybridoma, 13:215-9; Couto et al., 1995 Cancer Res. (Suppl.), 55, 5973s-7s; Werther et al., 1996 J. Immunol., 157:4986-95; O'Connor et al., 1998 Protein Engng 11:321-8).

Antibody fragments (as described), or part of a sequence or SEQ ID NO herein, are also encompassed. Such protein and/or polypeptide fragments can be "free-standing," or comprise part of a larger polypeptide or protein, of which the fragment forms a portion or region, e.g., a single continuous region of a SEQ ID NO: herein such as, e.g., connected in a fusion protein. Polynucleotides encoding such fragments are also encompassed.

Invention antibodies are engineered by any art-known method, such as, e.g., chemical synthesis; or recombinant, genetic, or molecular engineering and are not restricted by method of creation. Typically, nucleic acids encoding invention antibodies include an expression control polynucleotide sequence operably-linked to the encoding sequences, including naturally-associated or heterologous promoter regions. Preferably, expression control sequences are eukaryotic promoter systems in vectors that transform or transfect eukaryotic host cells, but control sequences for prokaryotic hosts can also be used. Once the vector is incorporated into an appropriate host cell, it is propagated under conditions suitable for expressing sequences, and, as desired, for the collection and purification of the light chains, heavy chains, light/heavy chain dimers, or intact antibodies, binding fragments or other immunoglobulin forms. Human constant region DNA sequences are isolated by art-known methods from a variety of human cells, but preferably from immortalized B-cells. Suitable source cells for the polynucleotide sequences and host cells for immunoglobulin expression and secretion are obtained from art-known sources.

The invention encompasses functional polypeptide sequences with substantial sequence similarity or identity to a sequence herein (e.g., at least: 87%, 88%, 89%, 90%, 91%, 92%, 93%, 94%, 95%, 96%, 97%, 98%, or 99% identical to an invention sequence (or fragment)) using art-known methods such as, e.g., optimizing residue matches. Such sequences include any with a functional characteristic of an invention antibody (e.g., binding and neutralizing mature human TGF-β1, -β2, and -β3 in a described assay herein). Such functionally related embodiments include additions, substitutions, and/or deletions of amino acid residues of an invention sequence in a CDR or a constant region. Amino acid substitutions and/or additions may be based on similarity in polarity, charge, solubility, hydrophobicity, hydrophilicity, and/or the amphiphatic nature of the residues involved. Also, non-classical amino acids or chemical amino acid analogs may be substituted or added into the polypeptide sequence. All such variants are in the scope of those skilled in the art of molecular biology given the teachings here specifying unique formulae or polypeptide sequences and the functional limitations of the invention.

Preferred embodiments of the invention composition have one or more of the following characteristics: $K_d$ less than $2 \times 10^{-13}$ M for TGF-β1, less than $5 \times 10^{-13}$ M for TGF-β2, less than $8 \times 10^{-3}$ M for TGF-β3; $k_{off}$ less than $8 \times 10^{-6}$ s$^{-1}$ for TGF-β1, less than $11 \times 10^{-6}$ s$^{-1}$ for TGF-β2, less than $13 \times 10^{-6}$ s$^{-1}$ for TGF-β3; k, greater than $5 \times 10^7$ M$^{-1}$s$^{-1}$ for TGF-β1, greater than $2 \times 10^7$ M$^{-1}$s$^{-1}$ for TGF-β2, and greater than $1.5 \times 10^7$ M$^{-1}$S$^{-1}$ for TGF-β3; $K_d$ improvement of a Fab composition for TGF-β1 with respect to a 1D11.16 Fab for TGF-β1 of at least 6000-fold; $K_d$ improvement of a antibody composition with respect to 1-D11.16 greater than about 34-fold for TGF-β1, greater than about 13-fold for TGF-β2, and greater than about 9-fold for TGF-β3; IC$_{50}$ greater than about 300-fold higher than of an IC$_{50}$ value of a 1D11.16 in an HT-2 assay; a ED$_{50}$ value in the range of about 11 to about 17 mg/kg in a U87MG human tumor xenograft model for the inhibition of Smad2 phosphorylation of (as described herein); less than 5.0% aggregation of an invention composition as determined by size exclusion chromatography after storage for 30 days at a concentration of 1 mg/mL, 40° C., in standard buffer (such as, e.g., Citrate (20 mM); Phosphate (10 mM); or PBS (10 mM phosphate, containing 150 mM NaCl)), and at pH (5.0, 6.5, or 7.4); less than 1% degradation products or no acidic forms—as determined by cation-exchange chromatography (CEX)—after storage for 30 days at 1 mg/mL, less than 35° C., in standard buffer (such as, e.g., Citrate (20 mM); Phosphate (10 mM) or PBS (10 mM phosphate, containing 150 mM NaCl)), and <pH7.0; and greater than 80% protein recovery of an invention composition using art-known methods after storage at a concentration of 2 mg/mL at 4° C. for two weeks, and dialysis recovery at pH 6.0.

Invention compositions are useful as therapeutics to modulate, treat, inhibit, ameliorate, or prevent a disease, disorder, state, syndrome, or condition associated with one or more of TGF-β1, and -β2, and -β3. Antibodies can be administered using any art-known method and may be combined for use with conventional pharmaceutically acceptable carriers, diluents, stabilizers, and excipients. These combinations can be placed into dosage forms such as by lyophilization in sealed dosage vials or under storage in stabilized aqueous preparations. Pharmaceutically acceptable carriers, diluents, stabilizers, and excipients are art-known or described, e.g., in the *Merck Index*, Merck & Co., Rahway, N.J.

In particular, antibodies (or fragments) of the invention are useful for treating cell proliferative disorders, including any disease, syndrome, disorder, condition, or state, affecting any cell, tissue, any site or any combination of organs, tissues, or body parts that is characterized by a single or multiple local abnormal proliferation of cells, groups of cells, or tissues, whether benign or malignant. As defined herein, a cell proliferative disorder encompasses, e.g., hematological malignancies (such as, e.g., MDS or MPD, such as, e.g., with megakaryocyte involvement (see, e.g., Sakamaki, et al., 1999 Blood 94(6):1961-70)), hairy cell leukemia and other hematological malignancies, such as, e.g., chronic myelogenous leukemia (CML), chronic lymphocytic leukemia (CLL), acute lymphoblastic leukemia (ALL), acute myelogenous leukemia (AML), etc.)); non-small cell lung cancer; breast cancer; prostate cancer (including hormone refractory); ovarian cancer; hepatocellular cancer; pancreatic cancer; multiple myeloma; colorectal cancer; a neoplasm of the colon, abdomen, bone, breast, digestive system, liver, pancreas, peritoneum, endocrine system (e.g., an adrenal gland, a parathyroid gland, the pituitary, the testicles, the ovary, the thymus, or the thyroid), eye, head, neck, nervous system (central or peripheral), the lymphatic system, pelvis, skin, spleen, thorax, and urogenital system. Additionally, an invention antibody is useful for skeletal muscle disease—such as, e.g., treatment of muscle wasting (e.g., cachexia); promotion of muscle growth (e.g., after disease, trauma, reconstruction, replacement).

A "chemotherapeutic agent" is a chemical compound useful in the treatment of cancer. Examples of chemotherapeutic agents include alkylating agents, such as cyclophosphamide and fluorouracil; antimetabolites, such as fluorouracil and gemcitabine; antibiotics, such as adriamycin; and antimiotic agents, such as vincristine and vinorelbine.

An "anti-angiogenic agent" refers to a compound that blocks, or interferes with, to some degree, the development of blood vessels. The anti-angiogenic agent may be, e.g., a small molecule or antibody that binds a growth factor or growth factor receptor involved in promoting angiogenesis.

The term "cytotoxic chemotherapy" as used herein refers to a substance that inhibits or prevents the function of cells and/or causes destruction of cells, including radioactive isotopes (e.g. $At^{211}$, $I^{131}$, $I^{125}$, $V^{90}$, $Re^{186}$, $Re^{188}$, $Sm^{153}$, $Bi^{212}$, $P^{32}$ and radioactive isotopes of Lu), and toxins such as small-molecule toxins or enzymatically active toxins of bacterial, fungal, plant or animal origin, including fragments and/or variants thereof.

A polynucleotide is "operably linked" when it is placed into a functional relationship with another polynucleotide. For example, a promoter or enhancer is operably linked to a coding sequence if it affects the transcription of the sequence. A peptide is "operably linked" to another peptide when the polynucleotides encoding them are operably linked, preferably they are in the same open reading frame.

The term "vector" includes a nucleic acid molecule capable of transporting another nucleic acid to which it has been linked including, but not limited to, plasmids and viral vectors. Certain vectors are capable of autonomous replication in a host cell into which they are introduced while other vectors can be integrated into the genome of a host cell upon introduction into the host cell, and thereby, are replicated along with the host genome. Moreover, certain vectors are capable of directing the expression of genes to which they are operably linked. Such vectors are referred to herein as "recombinant expression vectors" (or simply "expression vectors") and exemplary vectors are well known in the art.

As used herein, the expressions "cell," "host cell," "cell line," and "cell culture" are used interchangeably and include an individual cell or cell culture that is a recipient of any isolated polynucleotide of the invention or any recombinant vector(s) comprising a sequence encoding a HCVR, LCVR or monoclonal antibody of the invention. Host cells include progeny of a single host cell, and the progeny may not necessarily be completely identical (in morphology or in total DNA complement) to the original parent cell due to natural, accidental, or deliberate mutation and/or change. A host cell includes cells transformed, transduced or infected in vivo or in vitro with one or more a recombinant vectors or a polynucleotide expressing a monoclonal antibody of the invention or a light chain or heavy chain thereof. A host cell which comprises a recombinant vector of the invention (either stably incorporated into the host chromosome or not) may also be referred to as a "recombinant host cell". Preferred host cells for use in the invention are CHO cells (e.g., ATCC CRL-9096), NS0 cells, SP2/0 cells and COS cells (ATCC e.g., CRL-1650, CRL-1651), HeLa (ATCC CCL-2). Additional host cells for use in the invention include plant cells, yeast cells, other mammalian cells and prokaryotic cells.

Antibody Expression and Purification

To express an antibody of the invention, a DNA encoding a partial or full-length light and/or heavy chain are inserted into an expression vector such that the gene is operably linked to transcriptional and translational control sequences. The expression vector and expression control sequences are chosen to be compatible with the expression host cell used. The antibody light chain gene and the antibody heavy chain gene can be inserted into separate vectors or, more typically, both genes are inserted into the same expression vector. The antibody genes are inserted into the expression vector by standard methods. Additionally, the recombinant expression vector can encode a signal peptide that facilitates secretion of the anti-TGF-β monoclonal antibody light and/or heavy chain from a host cell. The anti-TGF-β monoclonal antibody light and/or heavy chain gene can be cloned into the vector such that the signal peptide is operably linked in-frame to the amino terminus of the antibody chain gene. The signal peptide can be an immunoglobulin signal peptide or a heterologous signal peptide.

In addition to the antibody heavy and/or light chain gene(s), a recombinant expression vector of the invention carries regulatory sequences that control the expression of the antibody chain gene(s) in a host cell. The term "regulatory sequence" is intended to include promoters, enhancers and other expression control elements (e.g., polyadenylation signals), as needed, that control the transcription or translation of the antibody chain gene(s). The design of the expression vector, including the selection of regulatory sequences may depend on such factors as the choice of the host cell to be transformed, the level of expression of protein desired. Preferred regulatory sequences for mammalian host cell expression include viral elements that direct high levels of protein expression in mammalian cells, such as promoters and/or enhancers derived from cytomegaloviris (CMV), Simian Virus 40 (SV40), adenovirus, (e.g., the adenovirus major late promoter (AdMLP)) and polyoma virus.

In addition to the antibody heavy and/or light chain genes and regulatory sequences, the recombinant expression vectors of the invention may carry additional sequences, such as sequences that regulate replication of the vector in host cells (e.g., origins of replication) and one or more selectable marker genes. The selectable marker gene facilitates selection of host cells into which the vector has been introduced. For example, typically the selectable marker gene confers resistance to drugs, such as G418, hygromycin, or methotrexate, on a host cell into which the vector has been introduced. Preferred selectable marker genes include the dihydrofolate reductase (DHFR) gene (for use in DHFR-minus host cells with methotrexate selection/amplification), the neo gene (for G418 selection), and glutamine synthetase (GS) in a GS-negative cell line (such as NS0) for selection/amplification.

For expression of the light and/or heavy chains, the expression vector(s) encoding the heavy and/or light chains is introduced into a host cell by standard techniques e.g., electroporation, calcium phosphate precipitation, DEAE-dextran transfection, transduction, infection and the like. Although it is theoretically possible to express the antibodies of the invention in either prokaryotic or eukaryotic host cells, eukaryotic cells are preferred, and most preferably mammalian host cells, because such cells, are more likely to assemble and secrete a properly folded and immunologically active antibody. Preferred mammalian host cells for expressing the recombinant antibodies of the invention include Chinese Hamster Ovary (CHO) cells (including DHFR-CHO cells, described in Urlaub and Chasin, *Proc. Natl. Acad. Sci. USA* 77:4216-20, 1980, used with a DHFR selectable marker, e.g., as described in Kaufman and Sharp, *J. Mol. Biol.* 159:601-21, 1982, and GS-CHO cells, described in Enosawa, et al., *Cell Transplantation* 6: 537-540, 1997, used with a glutamine synthetase (GS) selectable marker), NS0 myeloma cells, COS cells, and SP2/0 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the host cell and/or the culture medium using standard purification methods.

Host cells can also be used to produce portions, or fragments, of intact antibodies, e.g. Fab fragments or scFv molecules by techniques that are conventional. It will be understood by a skilled artisan that variations on the above procedure are within the scope of the present invention. For example, it may be desirable to transfect a host cell with DNA encoding either the light chain or the heavy chain of an antibody of this invention. Recombinant DNA technology may also be used to remove some or all the DNA encoding either or both of the light and heavy chains that is not necessary for binding to TGF-β. The molecules expressed from such truncated DNA molecules are also encompassed by the antibodies of the invention.

In a preferred system for recombinant expression of an antibody of the invention, a recombinant expression vector encoding both the antibody heavy chain and the antibody light chain is introduced into GS-CHO cells by electroporation. Within the recombinant expression vector, the antibody heavy and light chain genes are each operably linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Antibodies, or antigen-binding portions thereof, of the invention can be expressed in an animal (e.g., a mouse) that is transgenic for human immunoglobulin genes (see, e.g., Taylor, et al., *Nucleic Acids Res.* 20:6287-95, 1992).

Once expressed, the intact antibodies, their dimers, individual light and heavy chains, or other immunoglobulin forms of the present invention can be purified according to standard procedures of the art, including ammonium sulfate precipitation, ion exchange, affinity, reverse phase, hydrophobic interaction column chromatography, gel electrophoresis and the like. Substantially pure immunoglobulins of at least about 90%, 92%, 94% or 96% homogeneity are preferred, and 98 to 99% or more homogeneity most preferred, for pharmaceutical uses. Once purified, partially or to homogeneity as desired, the peptides may then be used therapeutically or prophylactically, as directed herein.

Composition

An antibody of the invention can be incorporated into pharmaceutical compositions suitable for administration to a subject. The compounds of the invention may be administered alone or in combination with a pharmaceutically acceptable carrier, diluent, and/or excipients, in single or multiple doses. The compositions for administration are designed to be appropriate for the selected mode of administration, and pharmaceutically acceptable diluents, carrier, and/or excipients such as dispersing agents, buffers, surfactants, preservatives, solubilizing agents, isotonicity agents, stabilizing agents and the like are used as appropriate. Said compositions are designed in accordance with conventional techniques as in e.g., *Remington, The Science and Practice of Pharmacy,* 19$^{th}$ Edition, Gennaro, Ed., Mack Publishing Co., Easton, Pa. 1995 which provides a compendium of formulation techniques as are generally known to practitioners.

A composition comprising an antibody of the invention may be administered to a subject exhibiting pathologies or disorders as described herein using standard administration techniques including intravenous, intraperitoneal, subcutaneous, pulmonary, transdermal, intramuscular, intranasal, buccal, sublingual, or suppository administration.

The route of administration of an antibody of the invention may be parenteral. Preferably, antibodies of the invention can be incorporated into a pharmaceutical composition suitable for parenteral administration. The term parenteral as used herein includes intravenous, intramuscular, subcutaneous, rectal, vaginal, or intraperitoneal administration. Peripheral systemic delivery by intravenous or intraperitoneal or subcutaneous injection is preferred.

The composition typically must be sterile and stable under the conditions of manufacture and storage in the container provided, including e.g., a sealed vial or syringe. Therefore, compositions may be sterile filtered after making the formulation, or otherwise made microbiologically acceptable. A typical composition for intravenous infusion could have a volume as much as 250-1000 ml of fluid, such as sterile Ringer's solution, physiological saline, dextrose solution and Hank's solution and a therapeutically effective dose, (e.g., 1 to 100 mg/mL, or more) of antibody concentration. Dose may vary depending on the type and severity of the disease. As is well known in the medical arts, dosages for any one subject depends upon many factors, including the patient's size, body surface area, age, the particular compound to be administered, sex, time and route of administration, general health, and other drugs being administered concurrently. A typical dose can be, for example, in the range of 0.001 to 1000 μg; however, doses below or above this exemplary range are envisioned, especially considering the aforementioned factors. The daily parenteral dosage regimen can be about 0.1

μg/kg to about 100 mg/kg of total body weight, preferably from about 10 μg/kg to about 5 mg/kg and more preferably from about 10 μg/kg to 3 mg/kg body weight per day. Progress may be monitored by periodic assessment. For repeated administrations over several days or longer, depending on the condition, the treatment is repeated until a desired suppression of disease symptoms occurs. However, other dosage regimens may be useful and are not excluded herefrom. The desired dosage can be delivered by a single bolus administration, by multiple bolus administrations, or by continuous infusion administration of antibody, depending on the pattern of pharmacokinetic decay that the practitioner wishes to achieve.

These suggested amounts of antibody are subject to a great deal of therapeutic discretion. The key factor in selecting an appropriate dose and scheduling is the result obtained. Factors for consideration in this context include the particular disorder being treated, the particular mammal being treated, the clinical condition of the individual patient, the cause of the disorder, the site of delivery of the antibody, the particular type of antibody, the method of administration, the scheduling of administration, and other factors known to medical practitioners.

Therapeutic agents of the invention may be frozen or lyophilized for storage and reconstituted in a suitable sterile carrier prior to use. Lyophilization and reconstitution can lead to varying degrees of antibody activity loss. Dosages may have to be adjusted to compensate. Generally, pH between 6 and 8 is preferred.

Articles of Manufacture.

In another embodiment of the invention, an article of manufacture containing materials useful for the treatment of the disorders or conditions described above is provided. The article of manufacture comprises a container and a label. Suitable containers include, for example, bottles, vials, syringes, and test tubes. The containers may be formed from a variety of materials such as glass or plastic. The container holds a composition of the invention which is effective for treating the disorder or condition and may have a sterile access port (for example the container may be an intravenous solution bag or a vial having a stopper pierceable by a hypodermic injection needle). The active agent in the composition is an anti-TGF-β antibody of the invention. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The following examples are offered for illustrative purposes only, and are not intended to limit the scope of the present invention in any way.

EXAMPLE 1

Antibody Production and Purification

For the simultaneous expression of the light chain and heavy chain of antibodies of the invention, both the genes encoding the heavy chain and light chain are cloned to form a double gene vector with each gene under the control of a separate hCMV-MIE promoter. The correct coding sequences are confirmed by DNA sequencing of both the light and heavy chain coding sequences.

The expression plasmid for the simultaneous expression of the light chain and heavy chain of an antibody of the invention is linearized by the single-cutting enzyme Sal I, precipitated with sodium acetate and ethanol, washed with ice-cold 70% ethanol, and air-dried in a sterile biosafety cabinet. The DNA pellet is then re-dissolved with the transfection medium and used to transfect CHO cells. Transfection is performed by electroporating the cell-DNA mixture using the GenePulsar (BioRad, Hercules, Calif.) set at 300 V and 1120 uFd. Clones of expressing an antibody of the invention are then generated by limiting dilution and further expanded for antibody production and purification. Antibodies of the invention are purified according to standard procedures of the art, including ammonium sulfate precipitation, ion exchange, affinity, reverse phase, hydrophobic interaction column chromatography, gel electrophoresis and the like.

EXAMPLE 2

ELISA

ELISA is run using Costar 3366 coated microtiter plates (overnight 4° C. with 0.4 ug/ml TGF-β1, TGF-β2, or TGF-β3). The plate is then washed (2×) before adding (100 uL) blocking solution (10 mg/ml BSA in wash buffer) per well. Fab dilutions are incubated in coated wells (1.5 hr, 22° C.). After washing, anti-human kappa-alkaline phosphatase conjugate is added and incubated (1 hr, 22° C.). A colorimetric substrate is added after extensive washing and absorbance measured (A560).

In another example, binding compositions are tested in a competitive ELISA assay. Typically, a solution phase assay is performed in which a compound that might compete with an antigen for binding to an antibody, such as an antibody, is combined first with the antibody in solution phase, then the degree of binding of the antibody with the antigen is subsequently measured. Materials: Carbonate coating buffer (50 mM sodium carbonate pH 9.6). Antigens: TGF-β1 (R&D Systems, Cat # 240-B/CF, 239 ug/ml), TGF-β2 (RDI, Cat #RDI-1035, 50 ug/ml), and TGF-β3 (RDI, Cat # RDI-1036/CF, 50 ug/ml) diluted to 0.4 ug/mL in coating buffer. Wash buffer (0.02 M Tris pH 7.4, 0.15 M NaCl, 0.1% Tween 20 and blocking solution of 10 mg/ml BSA (Sigma A-4503) dissolved in wash buffer). Proteins used as positive controls are mouse-anti-human TGF-β1, -β2, or -β3 (R&D Systems, cat# 1D11), mouse-anti-human TGF-β2 (R&D Systems, cat# BAF302) and mouse-anti-human TGF-β3 (R&D Systems, cat# BAF243), which are diluted to 1 ug/ml in block buffer. The detection antibody conjugate is anti-mouse kappa—peroxidase conjugate (Southern Biotech, cat# 1050-05), at a working concentration of 1:2000 in blocking solution. The color reaction substrate is O-phenylenediamine (OPD) tablets (Sigma cat# P-6912) dissolved in substrate buffer: 0.1 M $Na_2HPO_4$, pH to 5.0 with 0.05 M citric Acid. The OPD working solution (i.e., the volume for one 196-well-plate) is freshly made prior to each plate development by dissolving 1×5 mg OPD tablet in 12.5 mL of substrate buffer then by 5 ul of 30% $H_2O_2$. Protocol: A single 96 well plate is coated with antigen (TGF-β1, -β2, or -β3 at 0.4 ug/ml and dispensed 50 uL per well) tape-sealed and stored (16-20 h, 4° C.). The plate is washed (2×) in wash buffer before adding blocking solution (100 uL per well of 10 mg/ml BSA in wash buffer). After incubation (~1 hr-22° C.), the plate is washed (2×) with wash buffer then 100 uL of either sample (diluted in buffer) or control (diluted in PBS) is added per well and incubated (1.5 h-22° C.). After incubation, the plate is washed (6×) with wash buffer then either anti-mouse kappa-peroxidase conjugate (diluted to 1:2000 in Blocking solution) or SA-HRP (diluted 1:10,000 in blocking solution) added (100 uL/well). Test samples are left to incubate (1 h-22° C.) before adding 100 uL of OPD substrate/well. After color development (10 min), the 96-well plate is measured at an absorbance of 490 nm.

EXAMPLE 3

Kinetic Constants for Fabs

A KinExA 3000 instrument (Sapidyne Inst. Inc.) measures binding kinetics. Briefly, antigen is covalently-coupled to azlactone beads and the binding of an invention free Fab to the beads is detected on the instrument. To measure $K_d$, individual tubes containing 20 pM of Fab (200 pM for antibody) with decreasing serially diluted antigen (0-250 nM), is incubated (1-6d-25° C. in PBS containing 1% BSA, 0.02% azide and 0.01% Tween20). After incubation, free Fab in each equilibrated sample is determined on KinExA 3000 per manufacturer instructions. $K_d$ values are determined using KinExA 3000 software. To measure $k_{on}$, individual Fabs at 2 nM are mixed with 0-240 nM of antigen using the injection method according to manufacturer's instructions, and the unbound Fab is detected. The resulting data is used to calculate the $k_{on}$ with KinExA 3000 software. The $k_{off}$ is calculated using the formula $K_d=k_{off}/k_{on}$. Affinity data obtained under KinExA© conditions for Fab embodiments binding TGF Beta 1 are shown below in Table 1.

TABLE 1

| Fabs | $k_{on}$ (M$^{-1}$s$^{-1}$) (×10$^6$) | $k_{off}$ (sec$^{-1}$) calc, (×10$^{-6}$) | $K_d$ (pM) |
|---|---|---|---|
| Fab 3.A | 21.0 | 310 | 15 |
| Fab 4.17 | 22.0 | 6.0 | 0.28 |
| Fab 12.4 | 34.0 | 52 | 1.55 |
| Fab 12.7 | 3.7 | 0.34 | 0.09 |
| Fab 12.8 | 26.0 | 5.5 | 0.22 |

Similarly, Fab data for affinity binding of TGF-β2 under KinExA C conditions showed $K_d$<35 pM.

EXAMPLE 4

Kinetic Constants for Antibodies

Alternate methods of measuring kinetic constants are known, for example: affinity of an invention antibody for TGF-β1 (R&D Systems, Cat # 240-B/CF), TGF-β2 (RDI, Cat #RDI-1035), and TGF-β3 (RDI, Cat # RDI-1036/CF) is measured by BIAcore® 2000. Binding affinity measurements for full-length monoclonal antibodies of the invention are determined using Biacore. Except as noted, all reagents and materials are purchased from BIAcore® AB (Upsala, Sweden). All measurements made at room temperature. Samples are dissolved in HBS-EP buffer (150 mM sodium chloride, 3 mM EDTA, 0.01% (w/v) surfactant P-20, and 10 mM HEPES, pH7.4). Recombinant Protein A is immobilized on all four flow cells of a CM4 sensor chip at a level of 400-450 response units (RUs) using an amine coupling kit. Binding is evaluated using multiple analytical cycles. Each cycle is performed at a flow rate of 50 μL/min consisting of the steps: injection of 12 μL of antibody at 0.5 μg/mL, injection of 250 μL of TGF-β1 (starting at 5 nM and using two-fold serial dilutions to 0.13 nM for each cycle, with two injections for each concentration) followed by either a short (5 min) or long (120 min) delay for dissociation, and regeneration using two injections of 50 μL of 10 mM glycine hydrochloride, pH 1.5. Association and dissociation rates per cycle are made by fitting the biosensor data from a simple association model using ClampXP (Center for Biomolecular Interaction Analysis, Univ. of Utah) to extract the $k_{on}$ and $k_{off}$ rate constants; the equilibrium binding constant $K_d$ is calculated from $K_d=k_{off}/k_{on}$.

Full-length monoclonal antibodies of the invention were constructed by operably linked Fabs to an IgG$_4$ Fc region using standard technique: mAb 3.A comprising LC of SEQ ID NO:76 & HC of SEQ ID NO: 77; mAb 4.17 LC of SEQ ID NO:84 & HC of SEQ ID NO: 85; mAb 12.4 LC of SEQ ID NO:78 & HC of SEQ ID NO: 79; mAb 12.7 LC SEQ ID NO: 80 & HC SEQ ID NO:81; and mAb 12.8 LC SEQ ID NO:82 & HC SEQ ID NO: 83. When mAbs are measured using the described assay, the results are as stated in Table 2 below.

TABLE 2

| | | Average values | | |
|---|---|---|---|---|
| Mabs | Isoform | $k_{on}$ (M$^{-1}$s$^{-1}$) | $k_{off}$(s$^{-1}$) | KD (M) |
| Mab 12.4 | TGF-b1 | >4E+07 | 6.71E-06 | <2.0E-13 |
| | TGF-b2 | 2.42E+07 | 6.00E-06 | 2.65E-13 |
| | TGF-b3 | 1.76E+07 | 15.3E-06 | 8.51E-13 |
| Mab 12.7 | TGF-b1 | >5E+07 | 7.93E-06 | <2.0E-13 |
| | TGF-b2 | 2.80E+07 | 11.1E-06 | 4.73E-13 |
| | TGF-b3 | 1.56E+07 | 12.8E-06 | 8.20E-13 |
| Mab 12.8 | TGF-b1 | >5E+07 | 7.92E-06 | <2.0E-13 |
| | TGF-b2 | 2.29E+07 | 1.22E-05 | 1.00E-12 |
| | TGF-b3 | 1.85E+07 | 1.12E-05 | 5.40E-13 |
| Mab 3.A | TGF-b1 | >5E+07 | 1.07E-04 | <2.0E-12 |
| | TGF-b2 | >5E+07 | 2.18E-04 | <4E-12 |
| | TGF-b3 | 2.90E+07 | 2.38E-05 | 9.26E-13 |
| Mab 4.17 | TGF-b1 | >5E+07 | 9.71E-06 | <2.0E-13 |
| | TGF-b2 | 2.37E+07 | 9.86E-06 | 5.29E-13 |
| | TGF-b3 | 2.17E+07 | 2.84E-05 | 1.53E-12 |

EXAMPLE 5

Specificity

BIAcore is used to assess specificity of antibodies for entities, such as, e.g., the latent form of TGF-β1, -β2 or -β3. All measurements are performed at room temperature. Samples are dissolved in HBS-EP buffer (150 mM sodium chloride, 3 mM EDTA, 0.01% (w/v) surfactant P-20, and 10 mM HEPES, pH7.4). Recombinant Protein A is immobilized on all four flow cells of a CM4 sensor chip at a level of 400-450 response units (RUs) using an amine coupling kit. Binding is evaluated using multiple analytical cycles. Each cycle is performed at a flow rate of 100 μL/minute consisting of the following steps: injection of 15 μL of an antibody binding composition at 1 μg/mL, injection of 250 μL of either 5 nM TGF-β1, 5 nM latent TGF-β2, or 5 nM TGF-β3 followed by a short delay (5 min) for dissociation, and regeneration using two injections of 50 μL of 10 mM glycine hydrochloride, pH1.5. The amount of signal after capturing the antibody then ligand is determined using instrument control software. As the signal is proportional to the mass of protein captured, the stoichiometry of the captured ligand is readily calculable. Under such conditions, data for antibodies of the invention do not show significant specific binding of latent TGF isoforms.

EXAMPLE 6

HT-2 Cell Neutralization Assay

To test ability of an antibody to neutralize TGF-β bioactivity, one can adapt the HT-2 cell proliferation assay of Tsang, et al., (1995 Cytokine 7:389-97). The HT-2 assay assesses the neutralization characteristics of an antibody on the bioactivity of TGF-β by inhibiting and/or significantly diminishing the cell proliferation of the IL4-dependent HT2 cell line. Briefly, HT-2 cells proliferate in a dose dependent manner by IL-4 but undergo apoptosis by TGF-β. The TGF-β inhibition of proliferation is blocked by adding an anti-TGF-β antibody. Human HT-2 cells proliferate in response to IL-4 but TGF-β1, -β2, or -β3 inhibit IL-4-induced-proliferation. Consequently, an antibody is neutralizing if it prevents the normal inhibitory effect of TGF-β on IL-4-induced HT-2 cells. Accordingly, IL-4-induced cell proliferation should proceed unconstrained if sufficient amount of a TGF-β1, -β2, and -β3 specific binding composition is added to a mixture of HT-2 cells containing a cell proliferation inhibitory amount of TGF-β1, -β2, or -β3. The dose response neutralizing capability is made using the HT-2 assay in the presence of particular TGF-β isoforms and the IL-4 proliferation signal.

The degree of cell proliferation is determined using a commercial cell proliferation assay (e.g., CellTiter 96® AQueous One Solution Cell Proliferation Assay from Promega). HT-2 cells are maintained in RPMI 1640 supplemented with 10% FBS, penicillin/streptomycin (100 U/ml and 100 ug/ml respectively), 50 uM beta-mercaptoethanol and 10 ng/ml hIL-2 (R&D Systems). Cells are centrifuged at 1000 RPM in a Jouvan CR422 centrifuge and re-suspended in PBS. After washing (2×) with PBS, cells are finally re-suspended (0.15× $10^6$ cells/ml in Assay Media (phenol red-free RPMI 1640 supplemented with 2% FBS, penicillin/streptomycin (100 U/ml and 10 ng/ml respectively) and 50 uM beta-mercaptoethanol). To each well of a 96 well plate is added 50 ul of cells in Assay Media. Varying concentrations of an invention antibody are pre-incubated with recombinant TGF-β1, -β2, or -β3 (300 pg/ml in Assay Media). Following a 30 min pre-incubation, 50 ul of the TGF-β/antibody mixture is added to the HT-2 cells, followed immediately by 50 ul of Assay media containing 6.0 ng/ml murine IL-4 (2.0 ng/ml final). After incubation with the assay media (20-48 hr, 37° C. in a humidified, 5% $CO_2$ atmosphere), 35 ul of CellTiter 96 Aqueous solution (Promega Corp) is added. After further incubation (2-3 hr, as above), the assay is quantitated by analysis on an ELISA plate reader at 490 nM using the CellTiter 96® calorimetric assay (the quantity of formazan product—measured by amount of 490 nm absorbance—is directly proportional to the number of living cells). Compared to 1D11.16; ATCC-HB9849, antibodies of the invention exhibit improved neutralization of TGF-β1-, -β2-, and -β3-induced cell death and neutralization potency (e.g., IC50<0.1 mg/mL or <125 pM) as shown in Table 3 below.

TABLE 3

|  | mAb 3.A | | mAb 4.17 | | mAb 12.4 | | mAb 12.7 | |
| --- | --- | --- | --- | --- | --- | --- | --- | --- |
|  | Mean ng/ml | Mean ng/ml SEM | Mean ng/ml | SEM | Mean ng/ml | SEM | Mean ng/ml | SEM |
| TGF-β1 | 214.84 | 2.62 0.96 | 0.42 | 0.08 | 0.44 | 0.16 | 0.59 | 0.16 |
| TGF-β2 | 574.40 | 51.43 11.63 | 3.65 | 0.84 | 6.14 | 1.37 | 3.34 | 0.89 |
| TGF-β3 | 99.98 | 16.91 5.61 | 15.79 | 3.68 | 5.22 | 0.87 | 6.78 | 0.41 |

EXAMPLE 7

Xenograft Neutralization Assay

On binding TGF-βRI and TGF-βRII receptors, TGF-β ligands activate a signaling cascade, in which Smad-2 proteins are phosphorylated to produce downstream biologic effects such as, e.g., in cancer. Inhibition and/or significant diminishment of Smad2 phosphorylation evidences neutralization of TGF-β biological activities via transcriptional activation (see, e.g., Li, et al., 2005 World J Surg 29(3):306-11). To assess in vivo neutralization efficacy of an antibody, Phospho-Smad2 levels in a xenograft model and/or in multiple organs or tissue are made after exposure to an invention antibody to provide evidence of its neutralization efficacy in cell proliferative conditions such as, e.g., cancer. Testing in vivo efficacy is assessed by measuring the degree of phospho-Smad2 inhibition using a highly vascularized U87MG human tumor xenograft model (see, e.g., Plowman, et al., 1997 "Human tumor xenograft models" in Anticancer *Drug Development Guide: Preclinical Screening, Clinical Trials, and Approval*; Teicher B (ed) pp 101-25. Humana Press: Totowa N.J.). Female athymic nu/nu nude mice (Charles River, ~22-24 g) are quarantined and maintained (7d ad libitum food & water) before experimental manipulation. Testing starts by flank injections (s.c.) of subconfluent human U87MG glioblastoma cells (~5×$10^6$/per animal in 0.2 ml culture medium mixed with Matrigel (BD Biosciences, 1:1 v/v)) to promote tumor growth. Xenografts are then monitored until tumor volume reaches ~300 $mm^3$ then animals are randomly divided into treatment groups (10/group) with dosing initiated. Post-tumor implantation therapy starts when mAb 12.7 is administered (i.p.) at varying dosages (e.g., 1, 10, 100 ug/animal) in a saline vehicle twice a week (q4d) for a dosing duration of two weeks. Saline and human IgG4 controls (100 ug) are dosed in parallel. 48 H after last dose, animals are sacrificed with tumor and lung samples collected and snap frozen in liquid nitrogen. Samples are subsequently ground and lysed for Smad2 phosphorylation analysis by ELISA using antibodies against phosphorylated or total Smad2. Blood is also collected into EDTA-treated tubes via cardiac puncture. Blood samples are centrifuged to obtain plasma samples (800 rpm, 4° C., 30 min; then 3000 rpm, 4° C., 10 min), which are stored (−80° C.) until analysis. Statistical comparison of Smad2 phosphorylation is performed using JMP5.1 (SAS Institute). A one-way ANOVA and Dunnett's test with a control are also used. The phospho-Smad2 levels are assayed to evaluate target inhibition induced by treatment with invention compositions. The phospho-Smad2 level is normalized to total Smad (or total protein) to minimize variation introduced by tissue size and process handling. Data from this U87MG xenograft model show a dose dependent inhibition of Smad2 phosphorylation, thus demonstrating in vivo neutralization efficacy in modulating TGF-βeffects on cell proliferation. Data show that a 10 μg dose decreases Smad2 phosphorylation by 60% (p=0.012), with 72% inhibition achievable at doses of 100 μg (p<0.0001). Further, a 75% decrease in Smad2 phosphorylation is seen in lung tissue at 100 μg dose of an invention composition (p<0.001). There is also a dose-dependent decrease in Phospho-Smad2 levels (relative to total-Smad (T-Smad)) and decreased Phospho-Smad2 levels in lung tissue (at the 100 ug dose). Similar data obtain when phospho-Smad levels are normalized either to total Smad levels or to the square root of total Smad (tSmad) levels, thus, further indicating that percentage inhibition of tumor growth is correlated with increasing dosage delivery of an invention binding composition.

What we claim is:

1. A monoclonal antibody that binds TGF-Beta 1, 2, and 3, wherein each heavy chain variable region comprises the amino acid sequence shown in SEQ ID NO: 69, and each light chain variable region comprises the amino acid sequence shown in SEQ ID NO: 45.

2. A monoclonal antibody that binds TGF-Beta 1, 2, and 3, wherein each heavy chain comprises the amino acid sequence shown in SEQ ID NO: 81 and each light chain comprises the amino acid sequence shown in SEQ ID NO: 80.

3. A pharmaceutical composition, comprising said monoclonal antibody according to claim 1, and a pharmaceutically acceptable carrier, diluent, or excipient.

4. A pharmaceutical composition, comprising said monoclonal antibody according to claim 2, and a pharmaceutically acceptable carrier, diluent, or excipient.

* * * * *